US012558533B2

(12) United States Patent
Blum et al.

(10) Patent No.: US 12,558,533 B2
(45) Date of Patent: Feb. 24, 2026

(54) ELECTRONIC DRIVING CIRCUIT FOR SLEEVE FOR FES, NMES, AND/OR EMG READOUT, AND SLEEVE INCLUDING SAME

(71) Applicant: Battelle Memorial Institute, Columbus, OH (US)

(72) Inventors: Timothy M. Blum, Columbus, OH (US); Joshua R. Branch, Columbus, OH (US); Samuel Colachis, Columbus, OH (US); Amanda I. Noonan, Columbus, OH (US); John E. Bartholomew, Columbus, OH (US); Nicholas Annetta, Columbus, OH (US); Yelena Davis, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 459 days.

(21) Appl. No.: 18/017,899

(22) PCT Filed: Jul. 30, 2021

(86) PCT No.: PCT/US2021/043892
§ 371 (c)(1),
(2) Date: Jan. 25, 2023

(87) PCT Pub. No.: WO2022/026821
PCT Pub. Date: Feb. 3, 2022

(65) Prior Publication Data
US 2023/0277109 A1     Sep. 7, 2023

Related U.S. Application Data

(60) Provisional application No. 63/072,571, filed on Aug. 31, 2020, provisional application No. 63/058,776, filed on Jul. 30, 2020.

(51) Int. Cl.
*A61N 1/04* (2006.01)
*A61B 5/00* (2006.01)
(Continued)

(52) U.S. Cl.
CPC ............ *A61N 1/0484* (2013.01); *A61B 5/256* (2021.01); *A61B 5/296* (2021.01); *A61B 5/301* (2021.01);
(Continued)

(58) Field of Classification Search
CPC ... A61B 5/256; A61B 5/206; A61B 5/301304; A61B 5/313; A61B 5/389; A61B 5/397;
(Continued)

(56) References Cited

U.S. PATENT DOCUMENTS

| | | | |
|---|---|---|---|
| 2003/0144710 A1* | 7/2003 | Haugland | A61F 2/72 607/48 |
| 2013/0150697 A1* | 6/2013 | Imai | A61B 5/296 600/372 |

(Continued)

FOREIGN PATENT DOCUMENTS

WO     WO-2019043147 A1 *   3/2019

OTHER PUBLICATIONS

International Search Report of Application No. PCT/US2021/043892 Dated Oct. 26, 2021.

*Primary Examiner* — Eun Hwa Kim
(74) *Attorney, Agent, or Firm* — Lippes Mathias LLP

(57) ABSTRACT

A device for functional electrical stimulation (FES), neuro-muscular electrical stimulation (NMES), and/or in receiving electromyography (EMG) signals includes a sleeve and electrodes. The sleeve is sized and shaped to be worn on a human arm, and comprises a stretchable fabric The electrodes are secured with the sleeve and positioned to contact skin of the human arm when the sleeve is worn on the human
(Continued)

arm. An electronic circuit is configured to operate the electrodes. The electronic circuit includes relays connecting the electrodes with a stimulator for performing FES or NMES, and EMG readout circuitry connecting the electrodes with an EMG amplifier. The relays are closed during FES or NMES to connect the stimulator with the electrodes. The relays are open during EMG readout to isolate the stimulator from the EMG amplifier.

15 Claims, 17 Drawing Sheets

(51) Int. Cl.

| | |
|---|---|
| *A61B 5/256* | (2021.01) |
| *A61B 5/296* | (2021.01) |
| *A61B 5/301* | (2021.01) |
| *A61B 5/304* | (2021.01) |
| *A61B 5/313* | (2021.01) |
| *A61B 5/397* | (2021.01) |
| *A61N 1/36* | (2006.01) |

(52) U.S. Cl.
CPC .............. *A61B 5/304* (2021.01); *A61B 5/313* (2021.01); *A61B 5/397* (2021.01); *A61B 5/4836* (2013.01); *A61B 5/6824* (2013.01); *A61B 5/725* (2013.01); *A61N 1/0452* (2013.01); *A61N 1/0456* (2013.01); *A61N 1/0476* (2013.01); *A61N 1/36003* (2013.01); *A61N 1/36031* (2017.08); *A61B 2562/0209* (2013.01); *A61B 2562/046* (2013.01); *A61B 2562/182* (2013.01)

(58) Field of Classification Search
CPC ..... A61B 5/4836; A61B 5/6824; A61B 5/725; A61B 2562/0209; A61B 2562/046; A61B 2562/182; A61N 1/0484; A61N 1/0452; A61N 1/0456; A61N 1/0476; A61N 1/36003; A61N 1/36031
See application file for complete search history.

(56)                    References Cited

U.S. PATENT DOCUMENTS

| | | | |
|---|---|---|---|
| 2015/0148641 A1* | 5/2015 | Morun | ................... H05K 1/167 |
| | | | 600/372 |
| 2018/0093091 A1 | 4/2018 | Brodard | |
| 2018/0154140 A1* | 6/2018 | Bouton | ................ A61B 5/4836 |

* cited by examiner

| | Loose Ave | Snug Ave | Tight Ave |
|---|---|---|---|
| Wrist | -6% | 6% | 14% |
| 1/4 Arm | -12% | 0% | 10% |
| 1/2 Arm | -4% | 10% | 22% |
| 3/4 Arm | 6% | 19% | 33% |

% forearm location has the least amount of stretch across all arms

ELECTRONIC DRIVING CIRCUIT FOR SLEEVE FOR FES, NMES, AND/OR EMG READOUT, AND SLEEVE INCLUDING SAME

This application is a national stage entry under 35 U.S.C. § 371 of PCT/US2021/043892 filed Jul. 30, 2021, which claims the benefit of U.S. Provisional Application No. 63/072,571 filed Aug. 31, 2020 titled "STRETCHABLE FABRIC SLEEVE FOR FUNCTIONAL ELECTRICAL STIMULATION AND/OR ELECTROMYOGRAPHY", and which claims the benefit of U.S. Provisional Application No. 63/058,776 filed Jul. 30, 2020 titled "STRETCHABLE FABRIC SLEEVE FOR FUNCTIONAL ELECTRICAL STIMULATION AND/OR ELECTROMYOGRAPHY".

U.S. Provisional Application No. 63/072,571 filed Aug. 31, 2020 titled "STRETCHABLE FABRIC SLEEVE FOR FUNCTIONAL ELECTRICAL STIMULATION AND/OR ELECTROMYOGRAPHY" is incorporated herein by reference in its entirety.

U.S. Provisional Application No. 63/058,776 filed Jul. 30, 2020 titled "STRETCHABLE FABRIC SLEEVE FOR FUNCTIONAL ELECTRICAL STIMULATION AND/OR ELECTROMYOGRAPHY" is incorporated herein by reference in its entirety.

BACKGROUND

The following relates to the neuromuscular electrical stimulation (NMES) arts, functional electrical stimulation (FES) arts, electromyography (EMG) measurement arts, and to related applications such as rehabilitative or assistive systems, to virtual reality (VR) gaming user interfaces, augmented reality (AR) assistive system user interfaces, VR or AR systems employing such user interfaces, and to related arts.

EMG measurement entails measuring electromyography signals generated by musculature. EMG measurement devices are thus devices for receiving user input. That input may be volitional input, where the subject intentionally generates the EMG signals; or may be non-volitional input, for example a case in which a subject suffering from Parkinson's disease may involuntarily generate EMG signals due to pathological tremors. EMG signals may also include a combination of volitional and non-volitional signals, e.g. the aforementioned Parkinson's patient may generate volitional EMG due to intentional movement of an arm that is accompanied by non-volitional EMG due to tremors.

FES and NMES are techniques for applying electrical signals to musculature to generate somatosensory perceptions such as the sensation of being touched, sensation of heat, pain, pressure, or so forth; and/or to stimulate contraction of muscles. In VR or AR systems for gaming or other applications, such generation of somatosensory perceptions can enhance the immersive experience. For patients with muscle debilitation or paralysis due to stroke, spinal cord injury, or other pathology, stimulation of muscle contraction can provide a way to artificially recover muscle activity.

In such systems, the EMG signal readout or FES or NMES application is by way of surface electrodes contacting the skin, or by way of transcutaneous electrodes that penetrate the skin. Surface electrodes are advantageously non-invasive and are preferable or even mandatory in applications such as VR gaming where the user is unlikely to be willing to have electrodes implanted in order to play the game. A wearable sleeve with surface electrodes on the inside surface contacting the skin is a convenient and efficient way to quickly place a large number of electrodes onto the skin.

U.S. Pub. No. 2018/0154133 A1 published Jun. 7, 2018 and filed Jan. 16, 2018, titled "Neural Sleeve for Neuromuscular Stimulation, Sensing and Recording" is incorporated herein by reference in its entirety, and provides some nonlimiting illustrative examples of wearable sleeves with electrodes for NMES, FES, and/or EMG.

Disclosed herein are certain improvements.

BRIEF SUMMARY

In accordance with some illustrative embodiments disclosed herein, a device is disclosed for use in performing functional electrical stimulation (FES), in performing neuromuscular electrical stimulation (NMES), and/or in receiving electromyography (EMG) signals. The device comprises a sleeve and electrodes. The sleeve is sized and shaped to be worn on a human arm, and comprises a stretchable fabric. The sleeve has a distal end disposed on or adjacent a wrist of the human arm when the sleeve is worn on the human arm and a proximal end opposite from the distal end. The electrodes are secured with the sleeve and positioned to contact skin of the human arm when the sleeve is worn on the human arm. In some embodiments, the sleeve includes an inner sleeve that is in contact with the skin of the human arm when the sleeve is worn on the human arm, and an outer sleeve disposed over the inner sleeve when the sleeve is worn on the human arm. The inner sleeve has openings in which the electrodes are disposed.

In accordance with some illustrative embodiments disclosed herein, a method is disclosed for performing FES, NMES, and/or for receiving EMG signals. The method comprises: donning a sleeve comprising a stretchable fabric on a human arm, the donning including placing a distal end of the sleeve on or adjacent a wrist of the human arm and securing together edges of the sleeve along a length of the human arm to secure the sleeve on the human arm and to compress the sleeve around the human arm and to contact electrodes secured with the sleeve to skin of the human arm; and using the donned sleeve including at least one of: (i) energizing electrodes to perform FES or NMES on the human arm; and/or (ii) reading EMG signals produced by the human arm using the electrodes. The placing of the distal end of the sleeve on or adjacent the wrist of the human arm may include inserting a thumb of a hand attached to the human arm through a thumb loop disposed at the distal end of the sleeve.

In accordance with some illustrative embodiments disclosed herein, a device is disclosed for use in performing FES, in performing NMES, and/or in receiving EMG signals. The device comprises a sleeve and electrode assemblies. The sleeve is sized and shaped to be worn on a human arm. The sleeve has a distal end disposed on or adjacent a wrist of the human arm when the sleeve is worn on the human arm and a proximal end opposite from the distal end. The sleeve includes an inner sleeve that is in contact with the skin of the human arm when the sleeve is worn on the human arm, and an outer sleeve disposed over the inner sleeve when the sleeve is worn on the human arm. The electrode assemblies are connected to the inner sleeve. Each electrode assembly includes a circuit board and electrodes mounted on the circuit board. The circuit boards of the electrode assemblies are disposed between the inner sleeve and the outer sleeve, and the electrodes are inserted through openings of the inner sleeve to contact skin of the human arm when the sleeve is worn on the human arm.

In accordance with some illustrative embodiments disclosed herein, a device for functional electrical stimulation (FES), neuromuscular electrical stimulation (NMES), and/or in receiving electromyography (EMG) signals includes a sleeve and electrodes. The sleeve is sized and shaped to be worn on a human arm, and comprises a stretchable fabric The sleeve has a distal end disposed on or adjacent a wrist of the human arm when the sleeve is worn on the human arm and a proximal end opposite from the distal end. The electrodes are secured with the sleeve and positioned to contact skin of the human arm when the sleeve is worn on the human arm. The sleeve may include an inner sleeve contact with the skin and an outer sleeve disposed over the inner sleeve. The inner sleeve has openings in which the electrodes are disposed.

DETAILED DESCRIPTION

Figure 1:
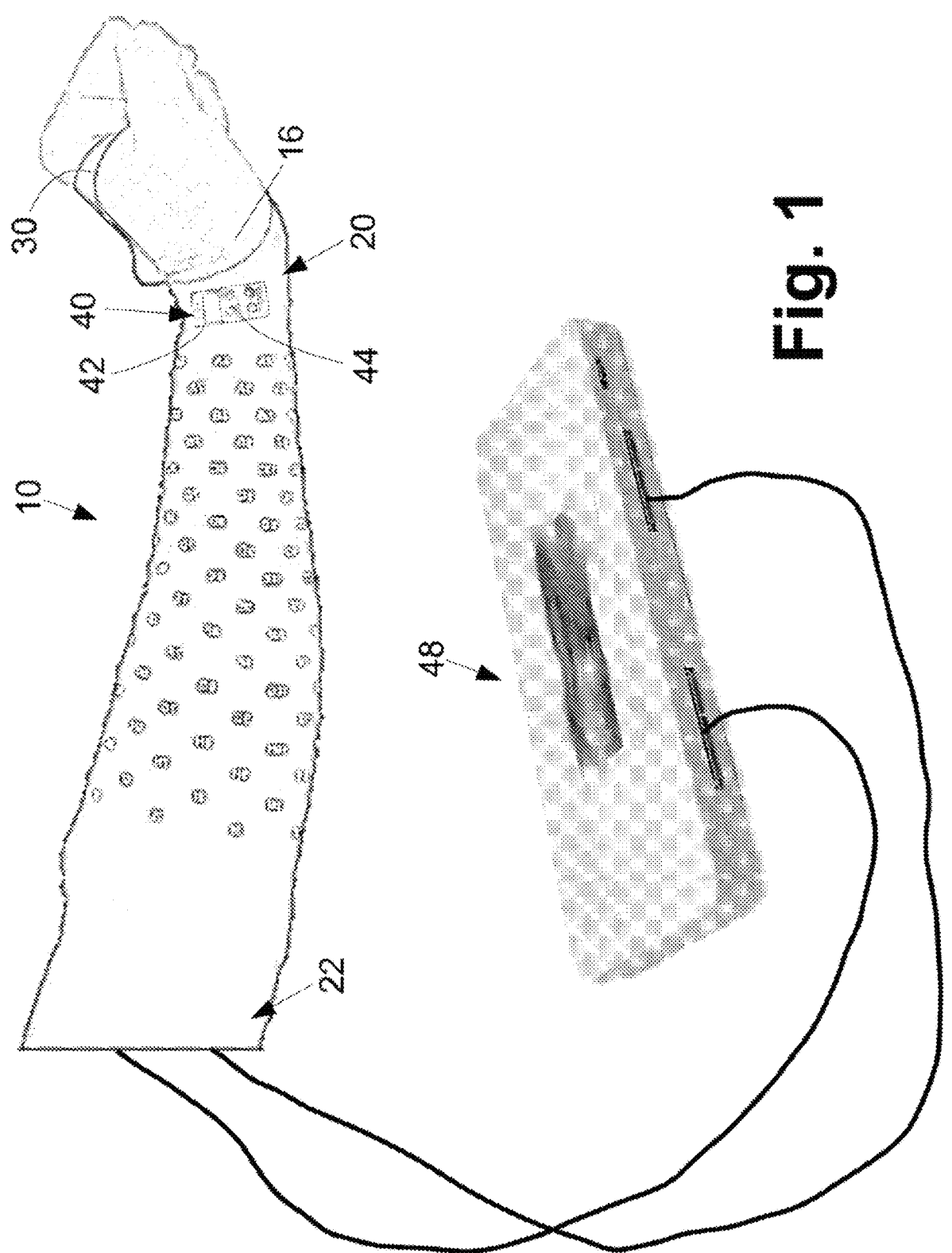
FIG. 1 diagrammatically illustrates a perspective view of a device for providing NMES or FES stimulation and/or EMG readout, in combination with driving/control hardware.

Disclosed herein are improved electrode sleeves for use in EMG, FES, and/or NMES. Various illustrative sleeves disclosed herein have certain advantages and/or solve certain problems which are outlined as follows.

One problem solved by various illustrative sleeves disclosed herein is difficulty in donning the sleeve. To be effective, an electrodes sleeve must provide for reliable electrical contact between the electrodes and the skin. High resistivity contact, or intermittent contact, can result in noisy EMG signals. For NMES and FES intended to stimulate muscle contractions, the applied NMES or FES signal can be large, e.g. on the order of 100-200 volts or higher with corresponding electrical current. Poor and/or intermittent electrical contact between an electrode and the skin at these high voltages can result in electrical arcing that can be painful and/or damaging to the skin.

Another problem solved by various illustrative sleeves disclosed herein is alignment of the sleeve on the arm. EMG signal interpretation is often dependent upon accurate mapping of the electrodes to the underlying musculature. Ideally, this is achieved by a priori knowledge of the mapping. However, if the sleeve positioning on the arm is imprecise or differs from one donning of the sleeve to the next, then this mapping is not constant. While post-acquisition processing can accommodate for some spatial shift due to imprecise or variable positioning of the sleeve, it is preferable to have the sleeve positioned as accurately as feasible. A related problem is changes in alignment subsequent to donning due to movement of the arm wearing the sleeve. Such movement can result in the positioning of the electrodes relative to the underlying musculature shifting.

Another problem solved by various illustrative sleeves disclosed herein is ease of donning the sleeve. For example, a VR gamer may want to don the sleeve by himself or herself, without assistance from anyone else. This means the VR gamer must don the sleeve on one arm using only the opposite arm and hand to assist and perform the donning. This concern is even greater for therapeutic or clinically assistive applications in which the subject has a debilitating pathology due to stroke, partial paralysis or the like, where the dexterity of the subject's opposite arm and hand may be impaired.

Another problem solved by various illustrative sleeves disclosed herein is maintenance. An electrodes sleeve is a relatively complex device, in which there may be dozens or even hundreds of surface electrodes secured to the inner surface of the sleeve. Failure of any of these electrodes results in degraded sleeve usability for EMG measurement or for FES or NMES. Such concerns are particularly significant for a reusable electrodes sleeve used by a VR gamer or by a medical subject at home, as the owner or user may want to launder the sleeve which can damage the electrodes. Furthermore, in such use scenarios there may be no way to repair damage to the electrodes sleeve on-site, so that the user or owner needs to ship the damaged electrodes sleeve to the manufacturer or other third party to effect repair.

Another problem solved by various illustrative sleeves disclosed herein is achieving a good fit of the sleeve to a particular user. A poor fit of the sleeve can create or exasperate many of the above-mentioned problems.

Another problem solved by various illustrative sleeves disclosed herein is the achieving of maximal coverage of the arm with surface electrodes. Such coverage can be limited by impediments such as fasteners that are used to secure the sleeve onto the wearer's arm.

Figure 2:
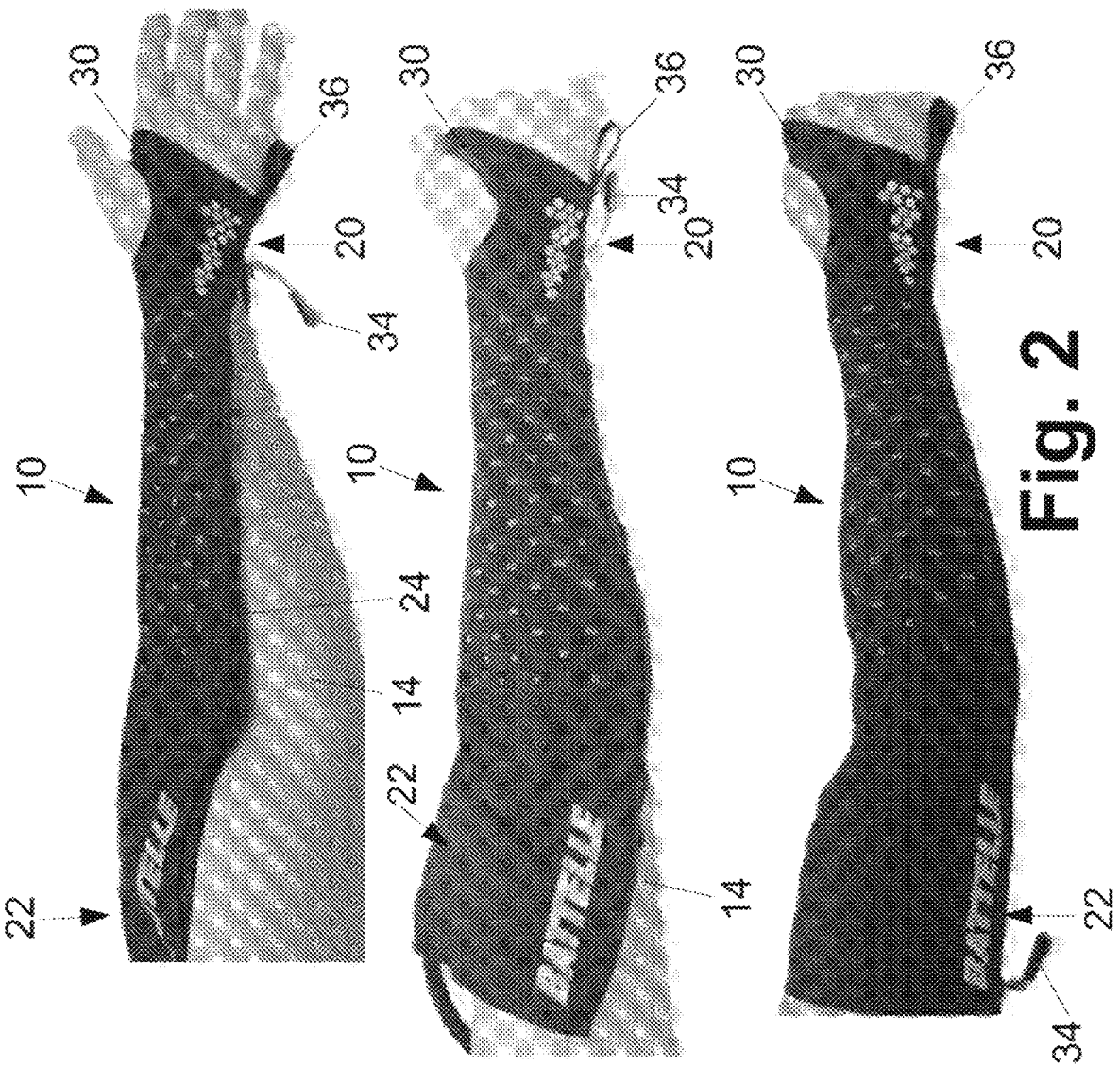
FIG. 2 illustrates a sleeve donning process.
Figure 3:
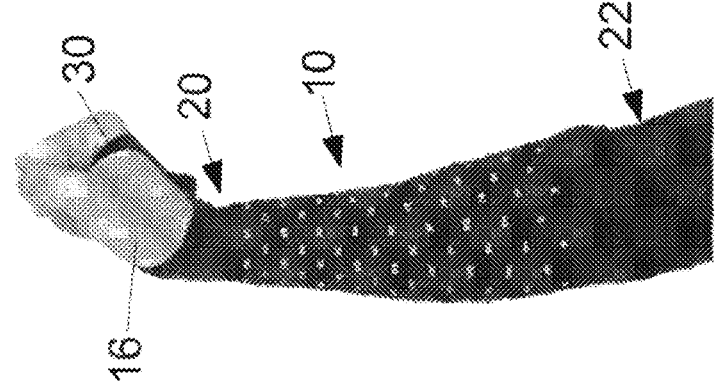
FIG. 3 illustrates flexibility of the donned sleeve.
Figure 3:
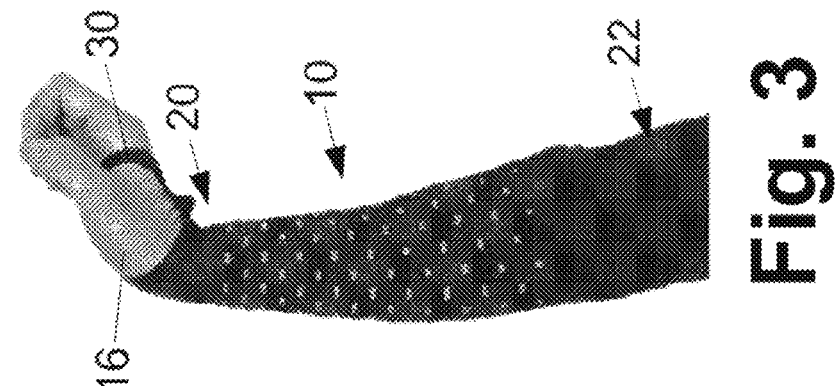
Figure 3:
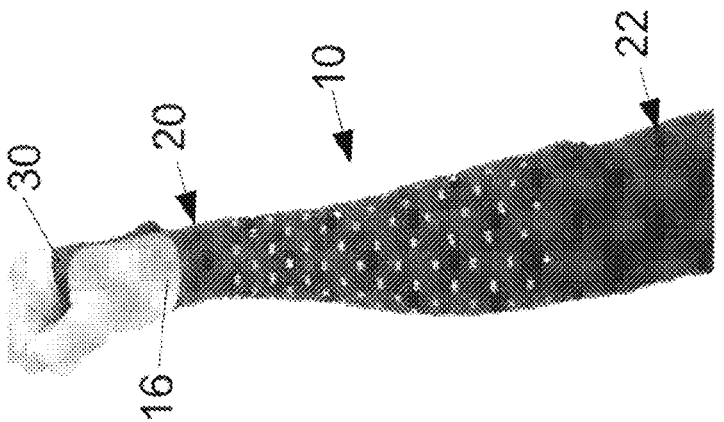
Figure 4:
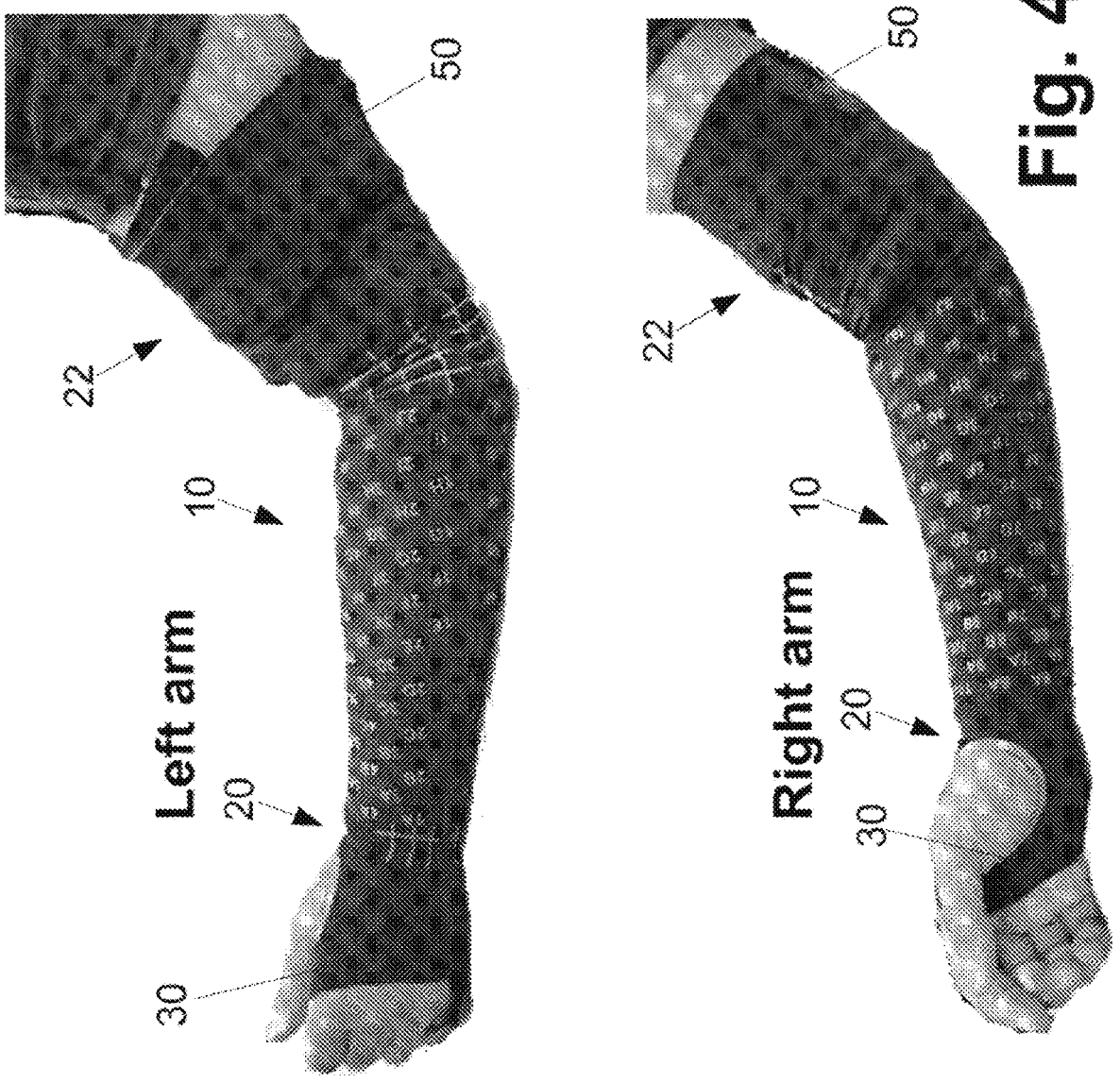
FIG. 4 illustrates reversibility of the sleeve.
Figure 5:
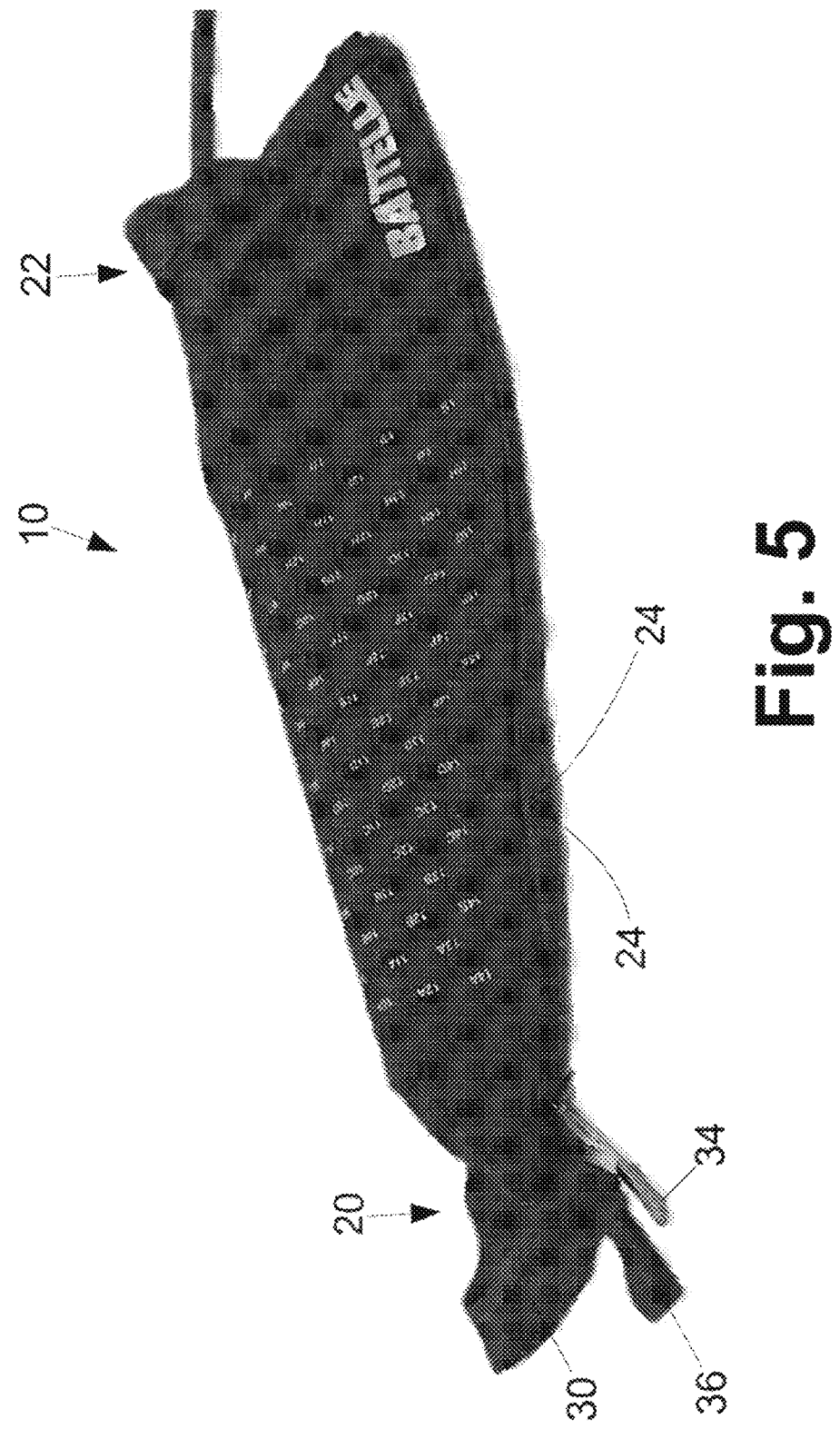
FIG. 5 illustrates a perspective view of the sleeve in isolation.
Figure 6:
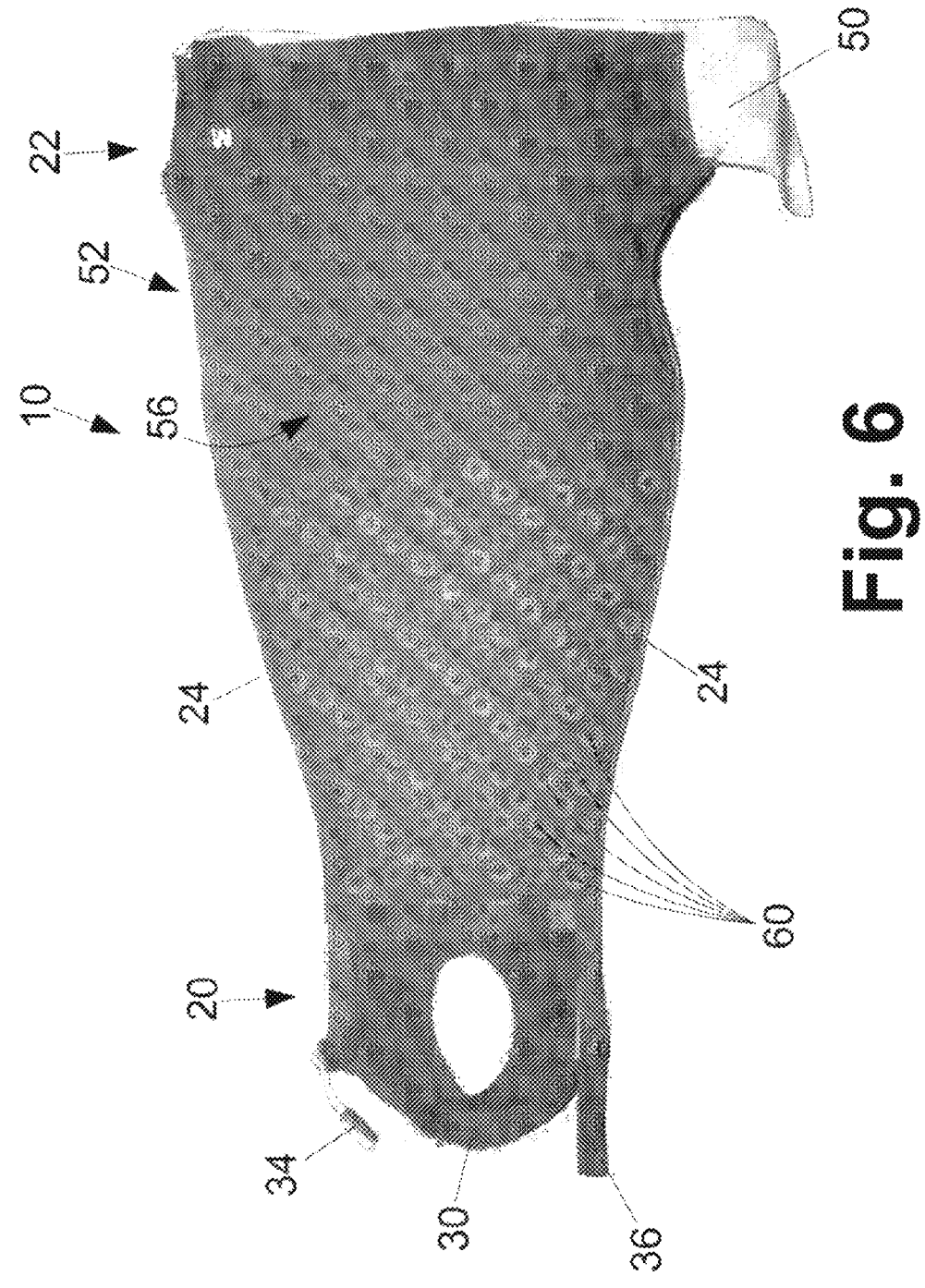
FIG. 6 illustrates the inside surface of the opened sleeve, without the electrodes installed.
Figure 7:
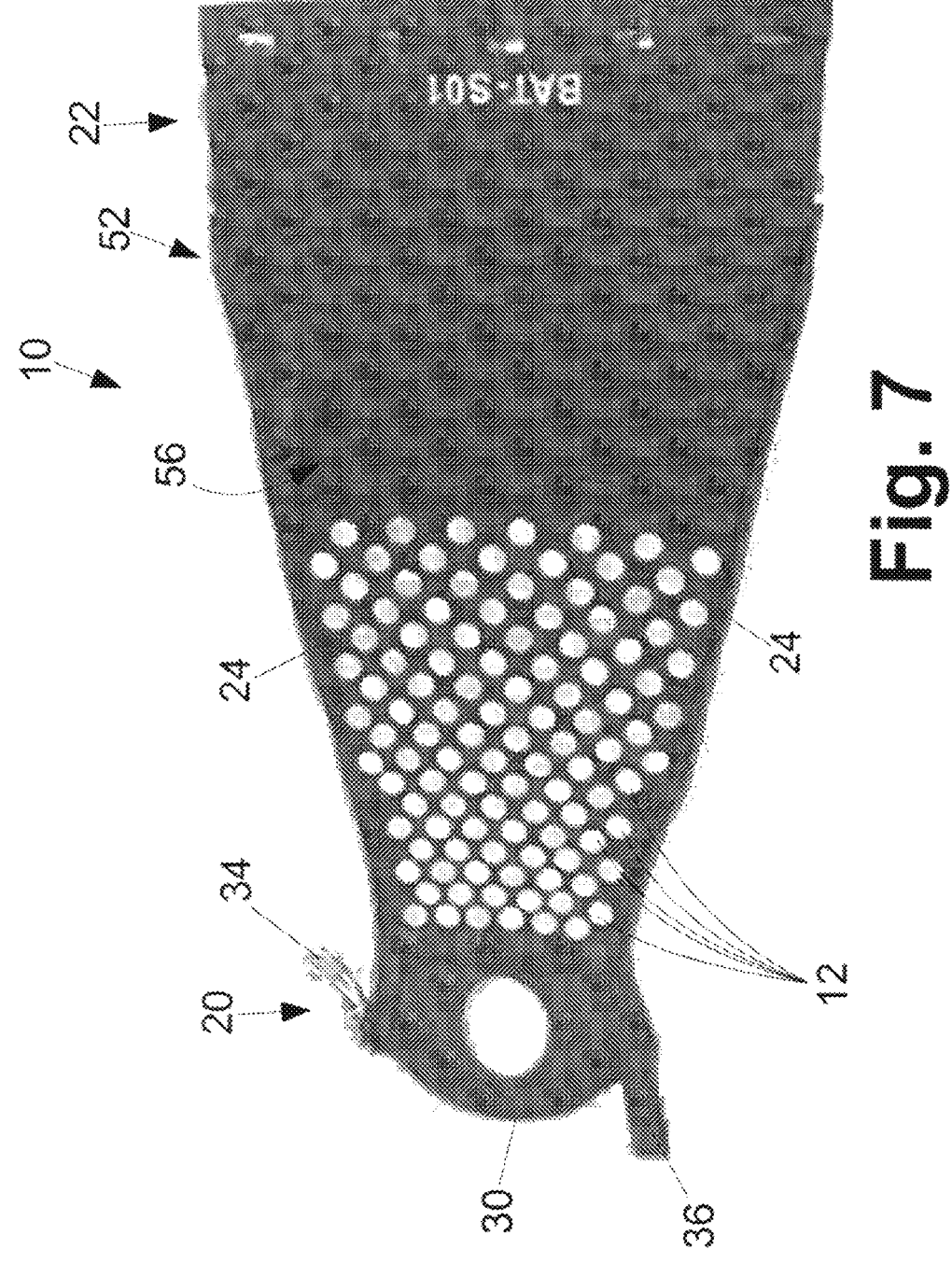
FIG. 7 illustrates the inside surface of the opened sleeve, with the electrodes installed.
Figure 8:
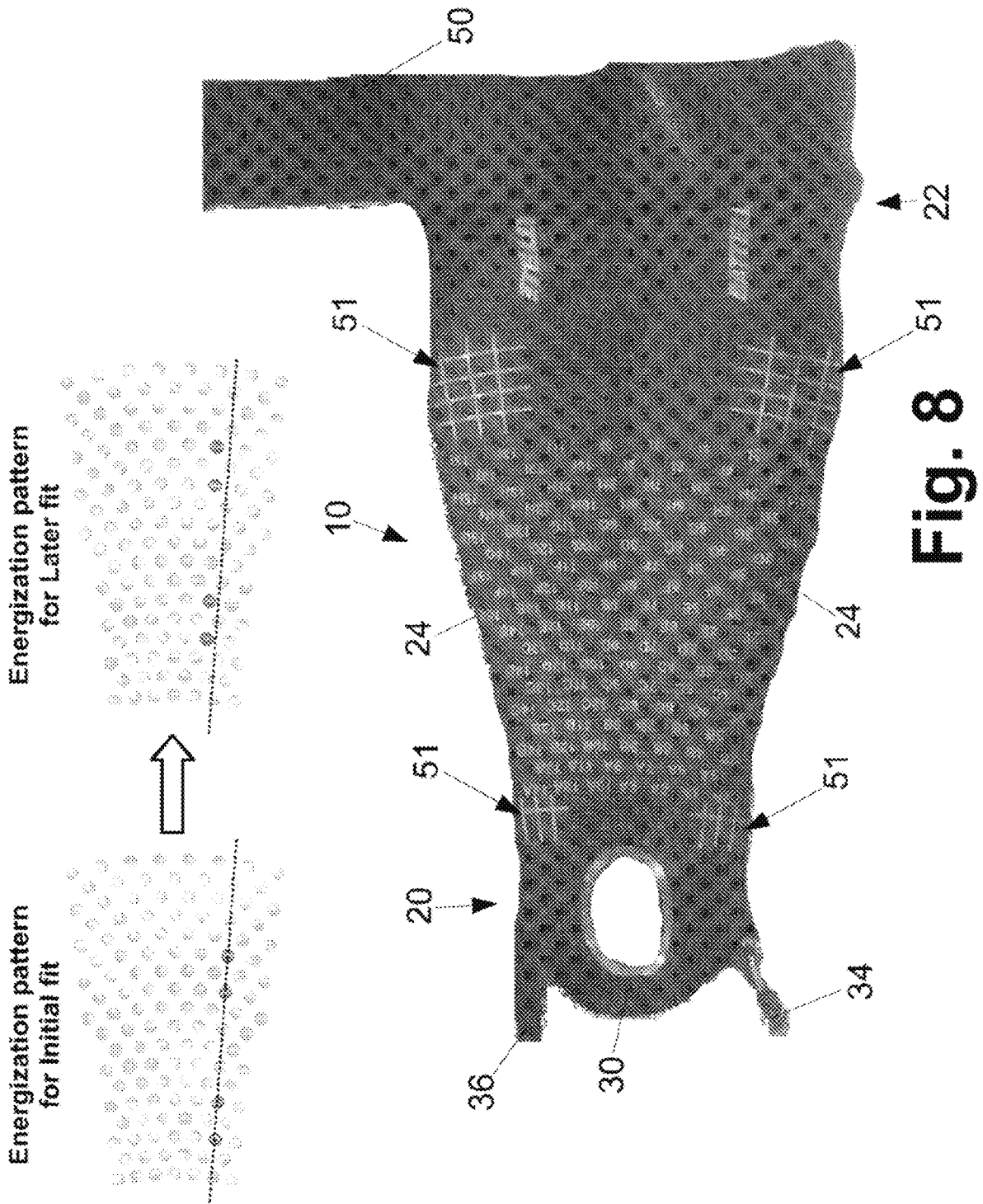
FIG. 8 illustrates the outside surface of the opened sleeve.

With reference to FIGS. 1-8, an illustrative device is shown for use in performing functional electrical stimulation (FES), in performing neuromuscular electrical stimulation (NMES), and/or in receiving electromyography (EMG) signals. The device includes a sleeve 10 and electrodes 12 (see FIG. 7). FIG. 1 shows a perspective view of the device in combination with driving/control hardware. FIG. 2 shows a sleeve donning process. FIG. 3 illustrates flexibility of the donned sleeve 10. FIG. 4 illustrates reversibility of the sleeve 10. FIG. 5 illustrates a perspective view of the sleeve 10 in isolation. FIG. 6 illustrates the inside surface of the opened sleeve 10, without the electrodes installed. FIG. 7 illustrates the inside surface of the opened sleeve 10, with the electrodes 12 installed. FIG. 8 illustrates the outside surface of the opened sleeve 10.

The sleeve 10 is sized and shaped to be worn on a human arm 14 (see sleeve donning sequence shown in FIG. 2), and comprises a stretchable fabric. In a suitable approach for selecting the fabric, a stretch percentage range was found that was deemed sufficient for electrode pressure at a minimum and wearer comfort at a maximum for each size. A parameter $L_{stretched}$ was the selected percentage. For a two-layer sleeve (see FIG. 10), two layers of the selected fabric were stretched over a ruler to determine a stretch range as follows:

$$\text{Stretch percentage} = \left(\frac{L_{stretched}}{L_{relaxed}}\right) \times 100\% \quad (1)$$

where $L_{relaxed}$ is the length of the two pieces of the fabric when in the relaxed state and $L_{stretched}$ is the length when stretched. In one embodiment, the stretch range was 7%-25% of the circumferential measurements of each size. This represents how much larger the circumferential measurement of a user's arm is over $L_{relaxed}$ at any given point along the sleeve. With this information, measurements can be taken for any potential patient/user (e.g., circumferential at 4 locations, see FIG. 15), enter them into a table, and calculate the stretch percentage of each size of sleeve on their arm at the four locations. The size is then recommended that falls in the 7-25% stretch range over most of the four measurement locations. When a user measures close to the extremes of this range, the smaller and/or larger size is tried as well, as appropriate. In some embodiments, the fabric of the sleeve 10 is an elastane fabric, such as spandex or lycra. Elastane fabrics comprise fibers of a long chain polyurethane, e.g. a polyether-polyurea copolymer.

Advantageously, a large stretch percentage (e.g. in the range 7% to 25% inclusive in some embodiments) allows for the sleeve 10 to be comfortably worn on the arm 14 while producing sufficient compression force against the electrodes 12 to ensure robust and continuous electrical contact between the electrodes 12 and skin of the human arm 14. In the illustrative embodiments, the fabric making up the sleeve 10 is assumed to have isotropic stretch in all directions. In other contemplated embodiments, the specified stretch factor (e.g. 7% to 25% inclusive) applies only in the circumferential direction, that is, in the direction of encircling the arm, as stretch in the circumferential direction provides most of the compressive force for ensuring electrical contact between the electrodes 12 and skin.

The sleeve 10 has a distal end 20 disposed on or adjacent a wrist 16 of the human arm 14 when the sleeve is worn on the human arm 14. The sleeve also has a proximal end 22 opposite from the distal end 20. The proximal end 22 is typically on the elbow or upper arm of the human arm 14 when the sleeve is worn on the human arm 14, with the precise placement depending upon the relative lengths of the sleeve and arm.

FIG. 2 illustrates the donning of the sleeve 10 on a human arm 14. The sleeve is split along its longitudinal axis extending between the distal end 20 and the proximal end 22, as best seen in the top view of FIG. 2. This forms longitudinal edges 24 of the sleeve 10, as labeled in the top view of FIG. 2 before the sleeve is secured on the arm 14, and as labeled in the "open" sleeve views shown in FIGS.

6-8. As used herein, the term "open" sleeve refers to the state in which the edges 24 of the sleeve are not joined together (e.g., FIGS. 6-8), while the term "closed" sleeve or "secured" sleeve refers to the state in which the edges 24 of the sleeve are joined together (e.g., FIG. 2 bottom view, and FIGS. 3 and 4). Hence, as seen in FIG. 2, the sleeve 10 is donned on the arm 14 by placing it over the arm 14 in the open position, and then securing together the edges 14. In the illustrative embodiments, the edges 24 include teeth of a zipper, and the edges 24 are secured together to close the sleeve 10 by closing the zipper having teeth on the edges 24 of the sleeve. Advantageously, closing the zipper in the case of an arm whose circumference is larger than the inside circumference of the relaxed sleeve 10 in the closed state causes stretching of the fabric of the sleeve 10 to accommodate the larger circumference of the arm, which produces a compressive force on the electrodes 12. While a zipper is advantageous, in other contemplated embodiments other types of fasteners may be used to secure together the edges 24 of the sleeve in the closed state of the sleeve 10, such as magnetic fasteners, buttons, or the like. In another contemplated fastener design, Velcro can be disposed on the edges of the sleeve 10 so that it can be secured by a press-and-fold over operation, instead of being zipped up. Such a Velcro fastener can also help the sleeve to be donned more tightly.

In general, the sleeve 10 is donned on the arm 14 by placing a distal end 20 of the sleeve on or adjacent the wrist 16 of the human arm 14, and then securing together edges 24 of the sleeve 10 along a length of the human arm 14 to secure the sleeve 10 on the human arm 14 and to compress the sleeve 10 around the human arm 14. As the electrodes 12 are secured on the inside of the sleeve 10 so as to be positioned to contact skin of the human arm 14 when the sleeve 10 is worn on the arm 14, the compression of the donned sleeve 10 applies force to the electrodes 12 secured with the sleeve 10 to press the electrodes 12 against the skin of the human arm 14, thereby making robust and constant electrical contact with the skin.

In a preferred embodiment, the density of electrodes 12 is higher in a distal region adjacent the distal end 20 than in a proximate region adjacent the proximal end 22. This is useful because there is a higher density of muscles, with smaller muscle sizes, in the distal region (i.e., including and/or adjacent the wrist 16) compared with the proximal region that is adjacent and/or includes the elbow region.

In some embodiments, the zipper (or, more generally, the edges 24 of the sleeve 10 when secured together to secure the sleeve 10 to the arm 14) is aligned with the ulna of the human arm 14 when the sleeve is worn on the human arm 14. This is advantageous because the zipper (or magnetic clasps, or other fasteners for securing together the edges 24 of the sleeve 10) present an area where electrodes cannot be present. The ulna is a long bone of the forearm that stretches from the elbow to the smallest (i.e. pinky) finger, and there is limited musculature disposed over the ulna. Hence, with the zipper (or more generally the secured edges 24) positioned over the ulna, the lack of electrodes in this area has limited or no effect on the FES or NMES that can be stimulated using the electrodes 12, and little or no effect on the EMG signals or map that can be acquired using the electrodes 12.

However, as previously noted, it can be difficult for a wearer to don the sleeve 10 by himself or herself, without the assistance of a second person. This is because the person donning the sleeve by himself or herself must do so using only the opposite arm (that is, the arm opposite the arm 14 on which the sleeve is being donned) for manipulation of the sleeve 10. To assist in donning of the sleeve, the illustrative sleeve 10 includes certain assistive features. A thumb loop 30 at the distal end 20 of the sleeve 10 is sized and positioned to receive a thumb 32 of a hand attached to the human arm a thumb loop at the distal end of the sleeve that is sized and positioned to receive a thumb of a hand attached to the human arm when the sleeve is worn on the human arm 14 when the sleeve is worn on the human arm. This allows the distal end 20 of the sleeve 10 to be held in position by the thumb when donning. In some embodiments, the zipper is operative to open the sleeve at the proximal end 22, but the zipper is not operative to open the sleeve at the distal end 20. This is best seen in the top view of FIG. 2 and in FIG. 5 (where the sleeve is folded over so the edges 24 are aligned for being zipped together, but have not yet actually been zipped together). As seen in FIGS. 2 and 5, in the open position the zipper does not open at the distal end 20. This eliminates the need for the person donning the sleeve 10 to perform the difficult task of "starting" the zipper by initiating engagement of the teeth on the two edges 24. (This is usually done by inserting an end pin on one side of the zipper into a receiving box on the other side of the zipper, which is an operation requiring substantial manual dexterity). In other embodiments, the zipper is fully separable, that is, the zipper is operative to open the sleeve at both the proximal end 22 and at the distal end 20. This is best seen in FIGS. 6-8, where the fully open zipper variant advantageously provides fuller access to the inside of the sleeve (see FIGS. 6 and 7). In either design, a pull loop or tab 34 is optionally provided to assist the wearer in drawing the zipper.

In some embodiments, a pinky finger loop 36 at the distal end of the sleeve is sized and positioned to receive a pinky finger of the hand attached to the human arm 14 when the sleeve 10 is worn on the human arm with the thumb received in the thumb loop 30. The optional pinky finger loop 36 provides further stability at the distal end 20 when donning the sleeve 10. As seen in the donning example of FIG. 2, the use of the pinky finger loop 36 (if provided) is optional, and it is not used in the donning example of FIG. 2.

With reference to FIG. 4, a further advantage of the design employing the thumb loop 30 (and optional pinky finger loop 36) is that it may be constructed to be reversible. That is, the (same) sleeve 10 with the thumb loop 30 is sized and shaped to be worn on either a left human arm (top of FIG. 4) or on a right human arm (bottom of FIG. 4).

With reference to FIG. 1, in some embodiments an optional secondary tensioner 40 (shown only in FIG. 1) is provided by which the sleeve can be further tightened. For example, the small diameter of the wrist can make the fit of the distal end 20 less tight than the fit of the rest of the sleeve 10. The secondary tensioner 40 can take any form, such in the illustrative example a first section 42 and a second section 44 both secured to the distal end 20 of the sleeve 10, in which the first section 42 can be folded and has projections, hooks, or the like that can connect with a chosen set of two (or more) available sets of receiving holes in the second section 44. Thus, the loosest fit at the distal end 20 is achieved by not using the secondary tensioner 40 at all, while progressively tighter fit at the distal end 20 can be achieved by engaging with successive sets of receiving holes in the second section 44. Alternatively, grip tape (not shown) can be placed at the wrist, elbow, and/or bicep to further secure the sleeve 10 on the arm. In another contemplated secondary tensioner configuration (not shown), tightening knobs can be provided that can be turned to draw the sleeve tighter, for example by pulling on tightening loops arranged circumferentially around the arm. When the secondary tensioner 40 is provide, then optionally pressure sensors may also be installed on the inside surface of the sleeve 10, which measure the tightness of the donned sleeve on the arms. Such pressure sensors can be used to determine when the donned sleeve 10 is sufficiently tight to provide good electrical contact between the skin and electrodes 12. More generally, the sleeve 10 may include small pouches or recesses containing pneumatic, hydraulic, piezoelectric, or other actuators that apply pressure/displacement to an area to enhance the sensation of the electrode stimulation.

With continuing reference to FIG. 1, an electronics module 48 is provided, which operates the sleeve 10 to perform FES, NMES, and/or readout of EMG. For FES or NMES, the electronics module 48 energizes selected subsets of the electrodes 12 to stimulate FES or NMES. The stimulation can result in muscle contraction leading to induced movement, or can produce somatostimulation so as to simulate a sensation of touch, heat, or the like. For EMG readout, the electronics module 48 reads voltages on the electrodes 12 to measure EMG produced by musculature of the arm 14. It is also noted that some of the electronics may be integrated into the sleeve 10, as will be further discussed.

As best seen in FIGS. 4, 6, and 8, in some embodiments the sleeve 10 includes a fastening loop 50 at the proximal end 22 of the sleeve 10. The fastening loop 50 encircles the human arm 14 at or proximate to the elbow or upper arm when the sleeve is worn on the human arm. In the illustrative example, the fastening loop including a hook-and-loop fastener. Again, this simplifies donning of the sleeve 10 for a person putting it on alone, or for a clinical patient with dexterity difficulties.

With reference particularly to FIG. 8, in some embodiments Cartesian alignment grids 51 are printed on the distal end 20 of the sleeve 10 and/or the proximal end 22 of the sleeve 10. These grids can be used to visually assess any shift between one fitting of the sleeve to a specific user to the next fitting. For example, the grids can have defined spacing (e.g. 1 cm) and in the initial fit the grid position can be determined with respect to an anatomical feature such as a finger line, elbow feature, or so forth. During the initial fit, electrode patterns are also determined to produce various stimulations, and/or electrode aligns various muscles or muscle groups for EMG reading are also determined. In a subsequent fit, the shift (if any) of the grid with respect to the anatomical feature can be visually determined, and this shift can be applied to the electrode patterns/alignments determined during the initial fit. These shifted electrode patterns/alignments can then be used for initial values in determining the electrode patterns/alignments for the subsequent fit. The upper right electrode layout diagrams shown in FIG. 8 diagrammatically illustrate this for a simple four-electrode energization pattern for FES or NMES.

Figure 9:
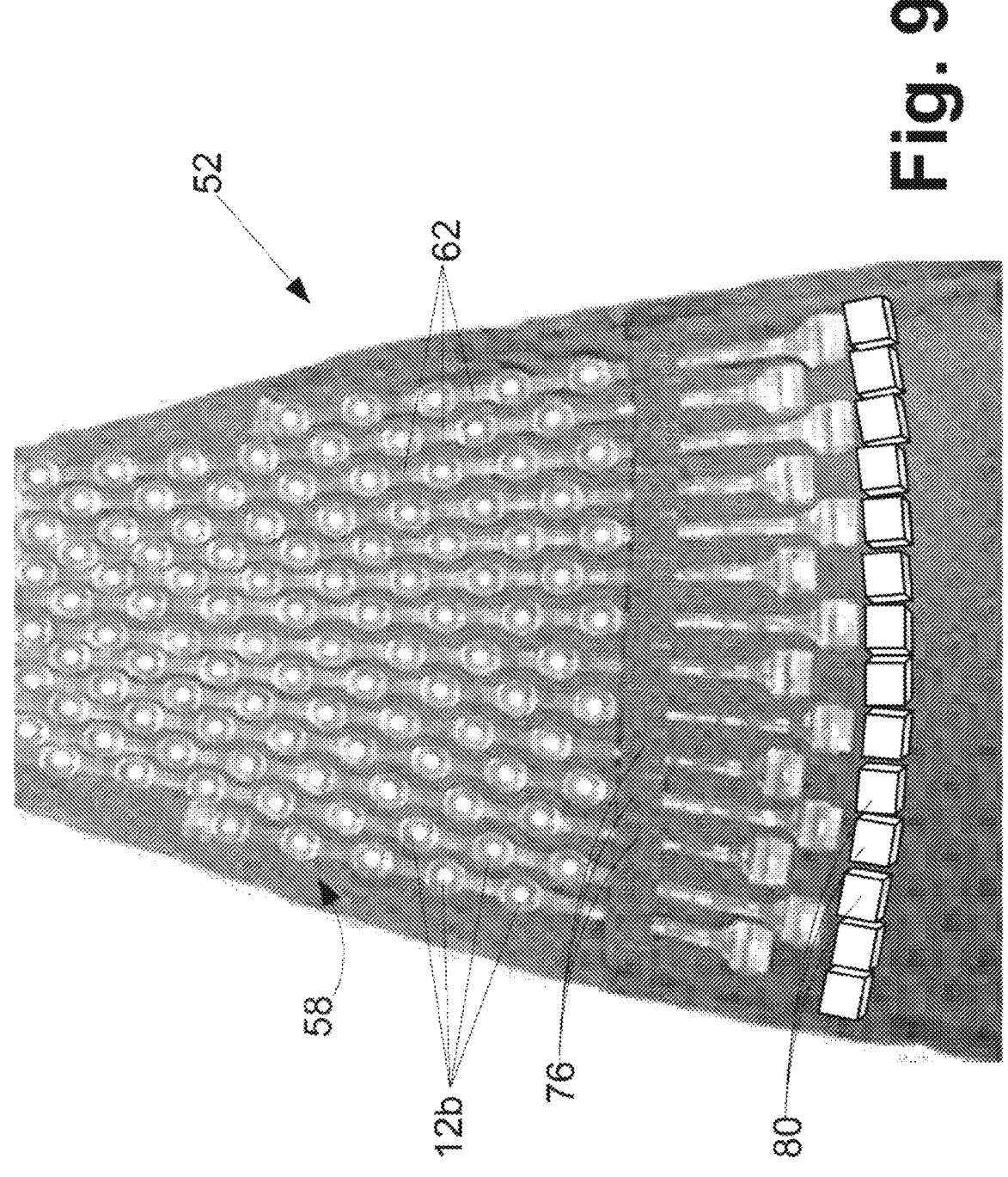
FIG. 9 illustrates the backside of the inner sleeve with electrode assemblies installed.
Figures 10, 11:
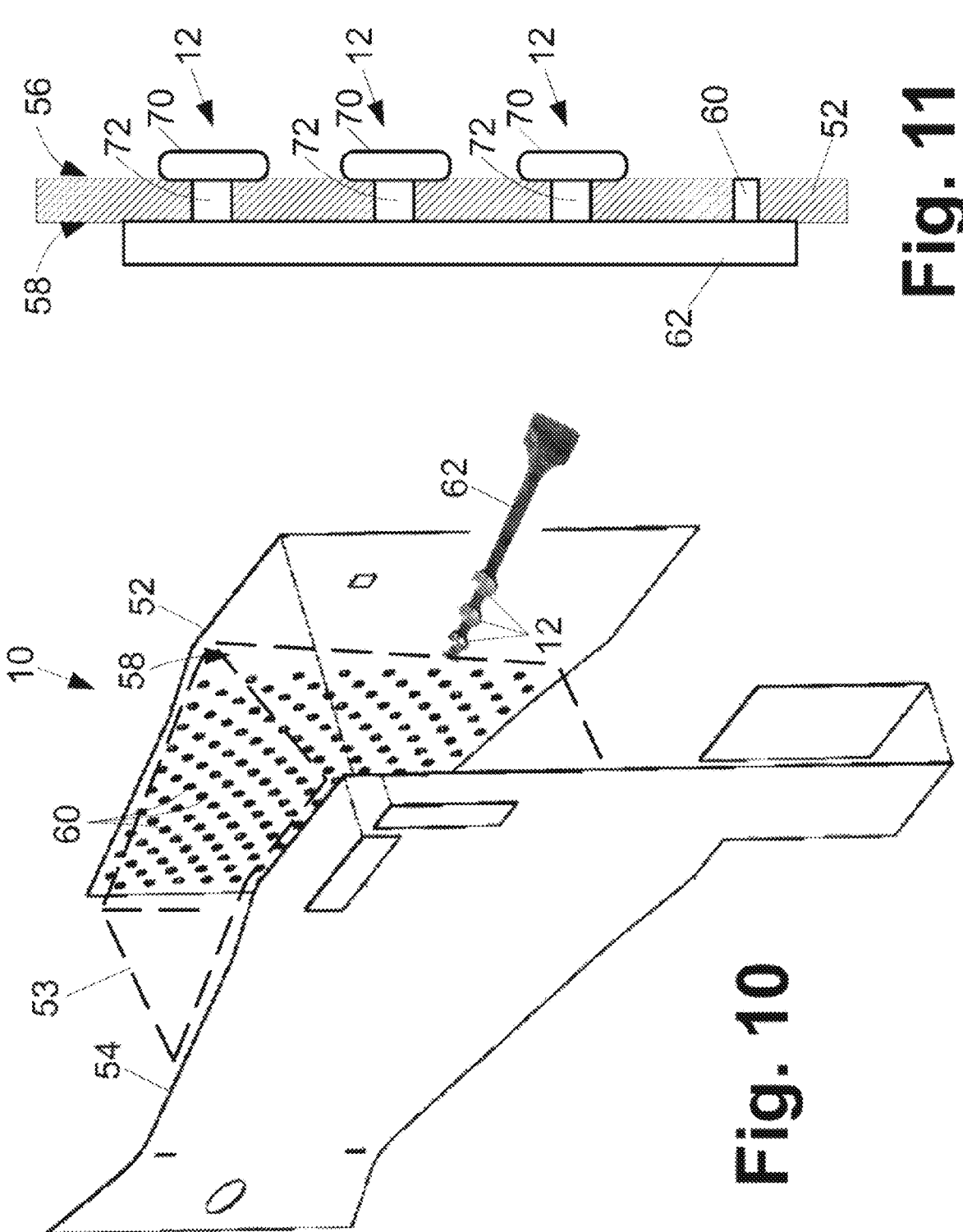
FIG. 10 diagrammatically illustrates an exploded perspective view of the inner and outer sleeves.
FIG. 11 illustrates a side-sectional view depicting the attachment of the electrodes to the inner sleeve.

With reference to FIGURES and with further reference to FIGS. 9 and 10, an illustrative implementation of the mounting of the electrodes 12 is described. As best seen in diagrammatic FIG. 10, the sleeve 10 in this embodiment includes an inner sleeve 52 that is in contact with the skin of the human arm when the sleeve 10 is worn on the human arm, and an outer sleeve 54 disposed over the inner sleeve 52 when the sleeve is worn on the human arm. The views of the open sleeve in FIGS. 6 and 7, as well as FIG. 9, depict the inner sleeve 52. More particularly, FIGS. 6 and 7 depict the exposed side 56 of the inner sleeve 52, that is, the side of the inner sleeve 52 that contacts the skin. FIG. 9 depicts the backside 58 of the inner sleeve 52, that is, the side 58 of the inner sleeve 52 that faces the outer sleeve 54. To further clarify, the exposed side 56 and the backside 58 are the two opposite principal sides of the inner sleeve 52.

As seen in FIGS. 6 and 10 which omit the electrodes 12, the inner sleeve 52 has openings 60. As seen in FIG. 7, the electrodes 12 are disposed in the openings 60. More particularly, in this embodiment the electrodes 12 are mounted on circuit boards 62 to form electrode assemblies that are connected to the inner sleeve 52. The circuit boards 62 of the electrode assemblies are disposed between the inner sleeve 52 and the outer sleeve 64 as diagrammatically shown in FIG. 10, and the electrodes 12 are inserted through the openings 60 of the inner sleeve 52 to contact skin of the human arm when the sleeve is worn on the human arm. FIG. 9 depicting the backside 58 of the inner sleeve 52 shows the circuit boards 62 and the backsides 12b of the electrodes (where the electrodes 12 are seen in FIG. 7 which shows the exposed side 56 of the inner sleeve 52). The openings 60 may be reinforced with hole reinforcements, e.g. a vinyl (or more generally electrically insulating) ring concentrically placed around each opening 60.

With reference to FIG. 11, a side-sectional view is shown depicting the attachment of the electrodes 12 to the inner sleeve 52. In this non-limiting illustrative implementation, the electrodes 12 comprise disk portions 70 and connecting portions 72 of narrower diameter than the disk portions 70. The connecting portions 72 are connected with the circuit board 62. Each electrode assembly comprising a circuit board 62 and the electrodes 12 mounted on the circuit board 62 (by way of connecting portions 72) is secured to the inner sleeve 52 at least in part by the electrodes 12 passing through the openings 60 of the inner sleeve 52. The elasticity of the inner sleeve 52 allows the opening 60 to expand to allow the disk portion 70 to pass through. Once through, the connecting portion 72 lies inside the opening 60 (which may be slightly expanded if the diameter of the connecting portion 72 is larger than the relaxed diameter of the opening 60), and the inner sleeve 52 is effectively secured between the disk portions 70 and the circuit board 62. For illustrative purposes, in FIG. 11 the bottommost opening 60 is left open (i.e. without an electrode disposed in it).

With returning reference to FIG. 9, in the illustrative example the circuit boards 62 are linear circuit boards each having a linear array of electrodes 12 mounted on the linear circuit board 62. In the illustrative example, in addition to the electrodes 12 passing through the openings 60 providing for securing the electrode assemblies 12, 62 to the inner sleeve 52, the inner sleeve 52 (and more particularly the backside 58 of the inner sleeve 52) further includes optional elastic loops 76 (further) securing the linear circuit boards 62 to the inner sleeve 52. The linear circuit boards 62 advantageously allow for high flexibility in the transverse gaps between the adjacent circuit boards 62 (i.e., the transverse gaps run lengthwise between the distal and proximal ends 20, 22). This allows the sleeve 10 to be wrapped around the arm 14, e.g. as shown in FIGS. 2-4. Preferably, the linear circuit boards 62 have some flexibility to permit deformation to align with the profile of the forearm. Optionally, the linear circuit boards 62 may be flex boards that are flexible, or stretch boards that are both flexible and stretchable. Such variants would further increase flexibility of the fabric sleeve 10.

To provide good electrical conductivity with the skin, the electrodes 12 can comprise hydrogel discs, or may be metal (e.g. steel) discs plated with an electrically conductive metal such as gold, palladium, or silver, or may comprise a compressible polymer and a conductive filler dispersed in the compressible polymer. The conductive filler may be, e.g., carbon fibers, carbon nanotubes (CNTs), or metallic particles. See U.S. Pub. No. 2018/0154133 A1 published Jun. 7, 2018. The conductive medium may be selected such that it becomes more tacky or sticky upon application of an electrical current, a change in temperature, a change in pH, or a change in moisture. See Id. The conductive medium can be a hydrogel, or a lotion, or a conductive polymer. See Id. In some embodiments, the conductive medium is more conductive in a z-direction and less conductive in either of a x-direction or a y-direction. See Id.

In other embodiments, the circuit boards 62 may be replaced by electrically conductive yarn or the like to provide flexible soft conductors for making electrical connection with the electrodes 12. For example, the electrodes can comprise a carbon nanotube (CNT)-based conductive medium shaped to form the electrodes 12 and conductive channels directly on the fabric of the sleeve 10. In this case, there are no steel electrodes. This could be achieved by printing, screening, or another method. In one approach, a conductive fabric sleeve is provided with a CNT-based sheet inner lining. Here, conductive fabric or interweaved copper is sewn into the sleeve 10 with protective insulation. In this embodiment, the circuit boards 62 can be omitted in favor of sufficient copper fibers to have a stable electrical connection. Surface electrodes could be formed and have a coating on the top of the overall sleeve 10 with the CNT or other dry electrode material (see description later herein) for ionic to electronic conduction enhancement.

In another embodiment, the electrodes 12 may comprise a material that becomes stickier when touched to the skin. For example, Poly(glycolic acid) (PGA), Poly(lactic acid) (PLA), or copolymers thereof above a certain temperature becomes solid and sticky. Addition of this material to electrode will allow for better adherence when the electrode touches the skin due to the increase in temperature of the electrode 12 caused by the contact with warmer skin.

In another embodiment, the electrodes 12 may comprise poly(3,4-ethylenedioxythiophene) polystyrene sulfonate (PEDOT:PSS) to allow for higher flexibility and tackiness.

In another embodiment, a dry electrode is formed as follows. A source of CNTs, such as a Tuball™ solution (marketed as a conductive additive for lithium ion batteries), is diluted by water (50:50 w/w) for an electrical conductor. Hyaluronic acid (HA) is added for an ionic conductor and acrylonitrile butadiene copolymer latex (NBR) for mechanical properties. Using a formulation for the sleeve at a loading of 5× HA to CNT's weight ratio is expected to work well for the electrodes 12, although other compositional ratios are contemplated. In general, addition of higher ionic conductor concentration such as 5× HA is expected to produce less pain due to intermittent conductivity. It is contemplated that such a dry electrode sheet could be fashioned to Velcro, zipper, or other structure(s) of the sleeve 10. The Velcro would line the CNT-based sheet border and be used to anchor the sheet to the sleeve 10. This would allow the CNT-based lining to be replaceable.

In some applications, both EMG and FES or other stimulation is to be performed. If using the same electrodes 12 for both EMG reading and FES, the electrodes cannot be optimized for either task. On the other hand, if different sets of electrodes are used for EMG and stimulation, respectively, (in other words, the electrodes 12 are divided into two sub-groups, one sub-group of electrodes for reading EMG and the other sub-group of electrodes for stimulation) then the electrode type can be optimized for these respective tasks. For example, the stimulation electrodes can be dry electrode CNT based electrodes; while, the EMG electrodes can be intertwined and have a dry electrode mixed with the Ag/AgCl coated conductive elastomer or other off-the-shelf electrodes for EMG. Locations of the EMG and stimulation electrodes can also optionally be optimized for the respective tasks. For example, neural signals at the fingers conduct from the upper arm, and if enough neural changes can be identified for movements like typing, then only an upper forearm EMG array may be employed.

With reference back to FIG. 10, the illustrative sleeve 10 includes an inner sleeve 52 that is in contact with the skin of the human arm when the sleeve 10 is worn on the human arm, and an outer sleeve 54 disposed over the inner sleeve 52 when the sleeve is worn on the human arm. Another contemplated approach for improving electrical conduction between the electrodes 12 and the skin is to add an air bladder 53 (shown diagrammatically by long-dashed lines only in FIG. 10) which is disposed in the gap between the outer sleeve 54 and the inner sleeve 52. After donning the sleeve 10, the air bladder 53 is inflated to provide further compression of the electrodes 12 against the skin. Optionally, pressure sensors may also be installed on the inner sleeve 52, which measure the compression of the inner sleeve 52 (and hence of the electrodes 12) against the skin. Such pressure sensors can be used to determine when the inflation of the air bladder 53 is sufficient to provide good electrical contact between the skin and electrodes 12.

With continuing reference to FIG. 9, in some embodiments a portion or all of the drive/control electronics for energizing the electrodes 12 (in the case of FES or NMES) and/or for reading EMG from the electrodes 12 is housed on-board the sleeve 10. In FIG. 9 this is by way of electronic modules 80, where each electrode assembly comprising a circuit board 62 and the electrodes 12 mounted on the circuit board is driven by a corresponding electronic module 80, which is connected with a connector at the proximal end of the circuit board 62 by wiring, a mating connector, or the like (feature not shown in FIG. 9). The electronic modules 80 may also be attached to the fastening loop 50, e.g. using Velcro® or another hook-and-loop fastener.

Figure 12:
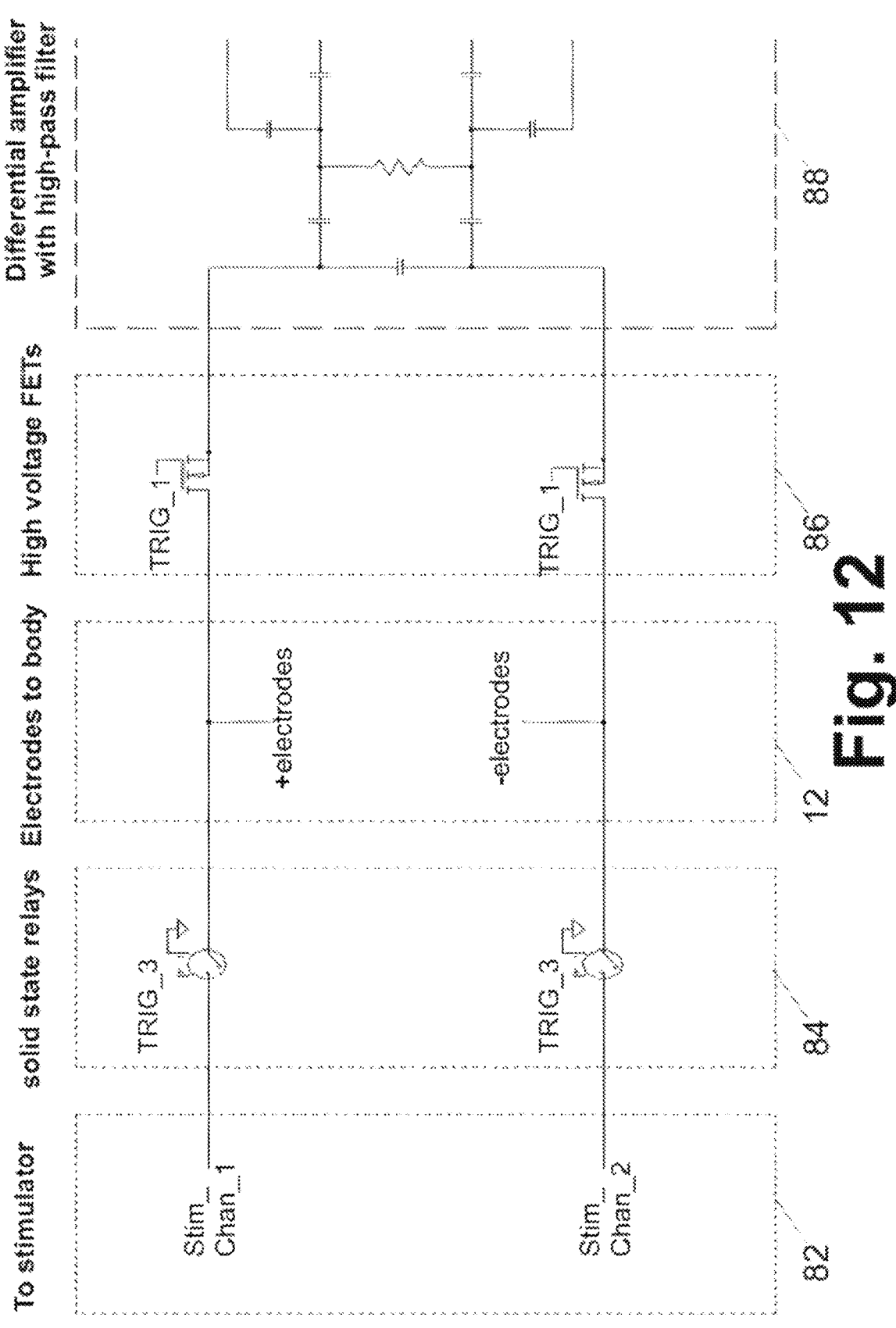
FIGS. 12, 13, and 14 illustrate an example of a drive/control electronic circuit suitable for stimulating FES or NMES and for EMG readout using the sleeve.
Figure 13:
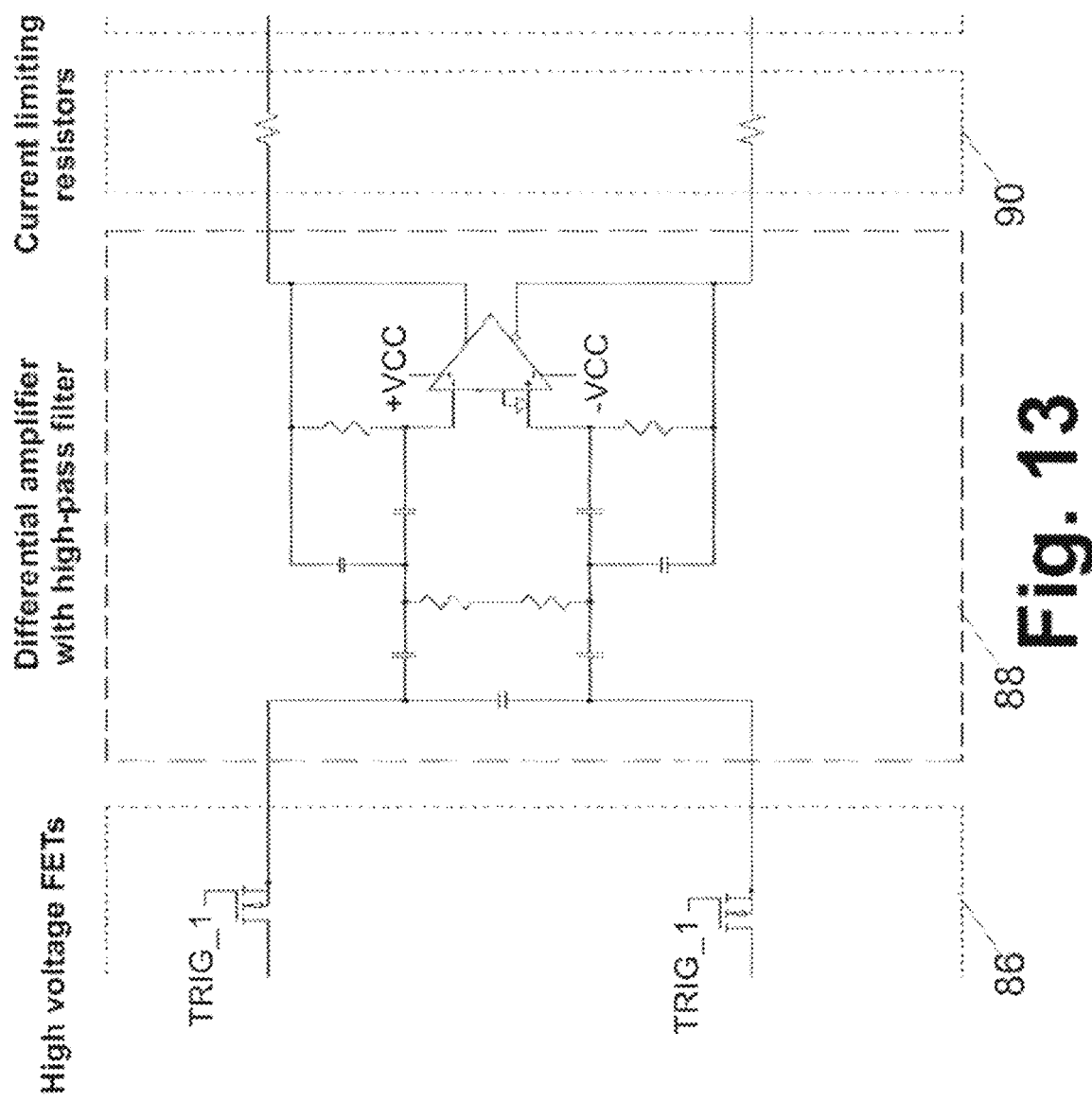
Figure 14:
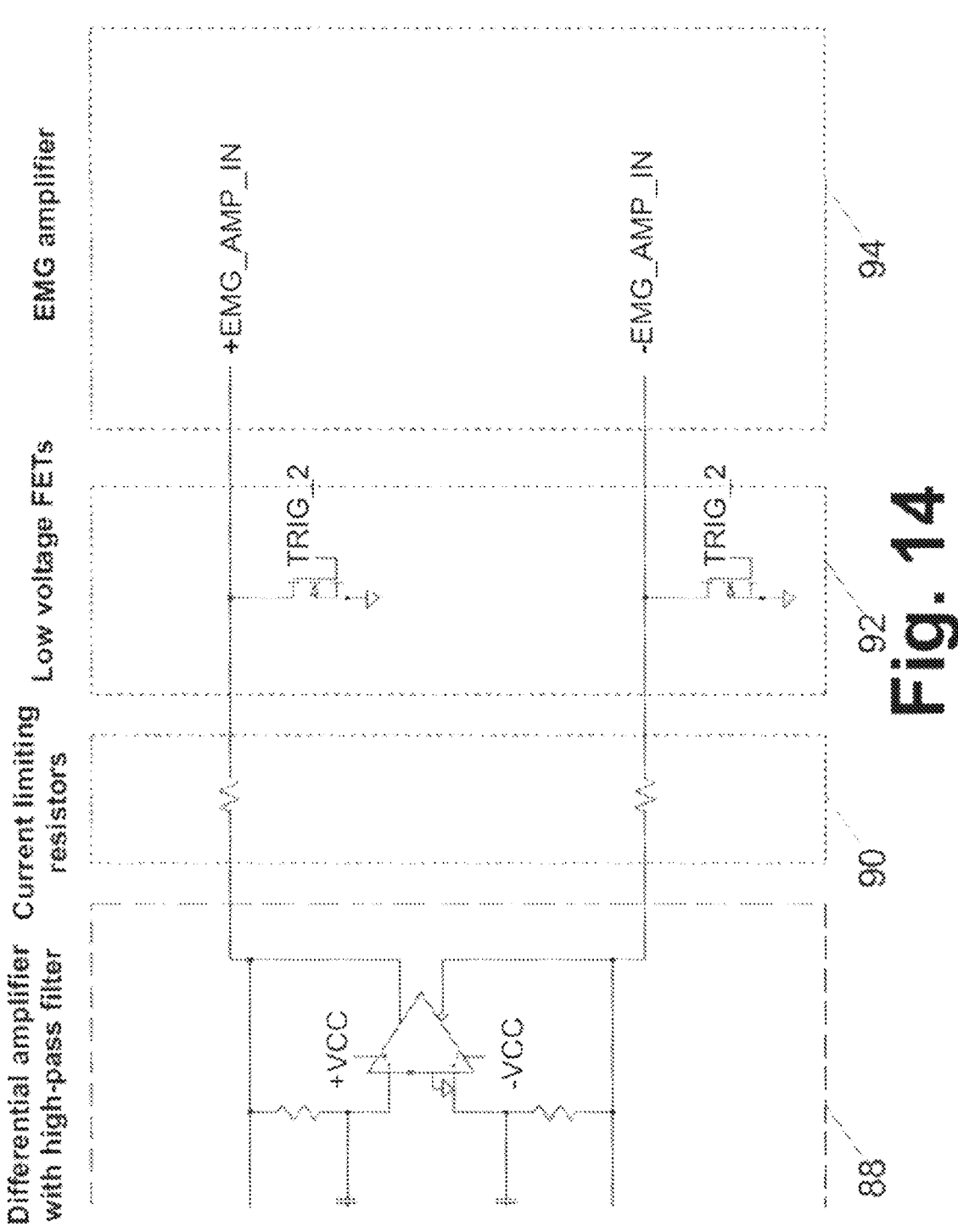

With reference to FIGS. 12, 13, and 14, a non-limiting illustrative example of a drive/control electronic circuit suitably housed (at least in part) in one of the electronic modules 80 is shown. It is noted that FIGS. 12, 13, and 14 illustrate a single electronic circuit, with some overlap to indicate the continuity. Specifically, FIG. 12 is cut off at the right side so as to depict only a left side of the differential amplifier with high-pass filter, which is shown in its entirety in FIG. 13; and similarly FIG. 14 is cut off at the left side so as to depict only a right side of the differential amplifier with high-pass filter, which again is shown in its entirety in FIG. 13.

The illustrative drive/control electronic circuit of FIGS. 12-14 provides for both EMG readout and electrical stimulation for NMES or FES. The electrodes 12 are diagrammatically indicated in FIG. 12. The sections 82, 84 of the circuit to the left of the electrodes 12 in FIG. 12 corresponds to the stimulation hardware. In one contemplated embodiment, the sections 82, 84 are not included in the electronic module 80 but rather are integrated into the external electronics module 48 shown in FIG. 1. The sections 86, 88, 90, 92, 94 to the right of the electrodes 12 in FIG. 12 and extending into FIGS. 13 and 14 corresponds to the EMG readout hardware. In one contemplated embodiment, the section 94 is internal to the external electronics module 48 shown in FIG. 1, and in the specific example of FIG. 14 the section 94 is implemented as an Intan EMG amplifier (available from Intan Technologies, Los Angeles, Calif., USA). This is merely an illustrative example. Optionally, the Intan EMG amplifier (i.e., the section 94 located at the bicep in the sleeve 10) is interfaced with off-the-shelf wireless INTAN hardware to provide wireless transmission of EMG signals off the sleeve 10. All of the hardware on the sleeve 10 would preferably be hidden at the bicep, and (at least for EMG only embodiments), there would be no cable.

During NMES or FES stimulation, the high voltage solid state relays of section 84 are closed to connect the stimulator to the electrodes 12, and the high voltage FETs (i.e. field-effect transistors) of section 86 are off to protect the EMG readout circuitry from the high voltages applied to the electrodes 12 by the stimulator (e.g. on the order of 100-200 volts or higher for some FES applications). The low voltage FETs of section 92 may also be on to pull the connected lines to ground to block any residual stimulation passing through the off high voltage FETs to further protect the EMG amplifier 94.

During EMG readout, the high voltage FETs of section 86 are on and the low voltage FETs of section 92 are off in order on to provide electrical continuity between the electrodes 12 and the EMG amplifier 94. The differential amplifier with high pass filter (section 88) is an optional component, but is provided to provide faster switching between the stimulation and EMG readout phases and to remove common mode noise.

In general, the high voltage applied during surface FES tends to cause EMG hardware to saturate, such that EMG recordings cannot be made for a long period of time (>25 ms) after each stimulation pulse. Even more, the high voltage applied during surface FES can damage the EMG hardware. The illustrative drive/control electronic circuit of FIGS. 12, 13, and 14 addresses this problem as follows. Solid state relays 84 operate to disconnect the stimulator from the electrodes to reduce noise coupling. High voltage FETs 86 block the high voltage stimulation from getting to the low voltage EMG hardware. Low voltage FETs 92 clamp the EMG inputs to ground during the stimulation pulse. An active, differential, high pass filter 88 speeds up the recovery of the EMG signal to baseline after the stimulation pulse. The above hardware can be placed on the front-end 94 of an Intan amplifier and data acquisition hardware which allows for high channel count. The hardware is in a small form factor such that it can fit into a sleeve. This solution protects the EMG hardware and reduces the dead time in the EMG data to about 12.5 ms in some embodiments.

Optionally, the electrodes 12 may include electrostatic discharge (ESD) suppressors (not shown), for example implemented as back-to-back Zener diodes, connected to protect the electrodes from electrostatic discharge. The high voltage solid state relays of subcircuit 84 serve as a connect/disconnect subcircuit for the stimulation channels. Optionally, optical control (not shown) of the high voltage solid state relays of section 84 is performed by way of LEDs or other light emitters 96 (not shown) to provide optoisolation. The high pass filter of section 88 expedites recovery between the stimulation and EMG readout phases. Various types of high pass filters can be used. In one embodiment, the high pass filter may be implemented as a Chebyshev filter, for example that operates at approximately 200 Hz in one specific example, although other frequencies are contemplated. Subcircuit 92 comprises low voltage FETs providing short to ground during the stimulation phase to protect the EMG readout circuitry. Section 94 diagrammatically depicts connection to an Intan EMG amplifier.

Figure 15:
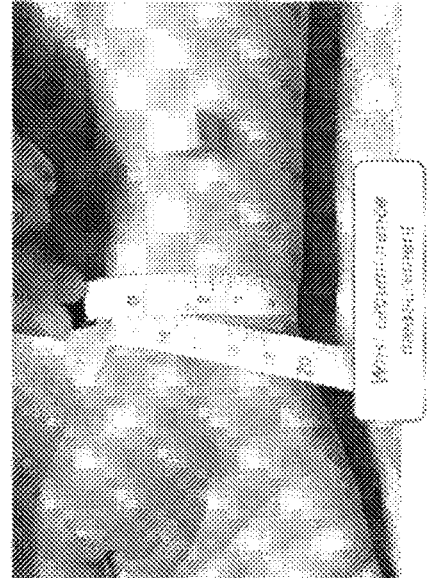
FIG. 15 illustrates measurements for sizing a sleeve for a specific user.
Figure 15:
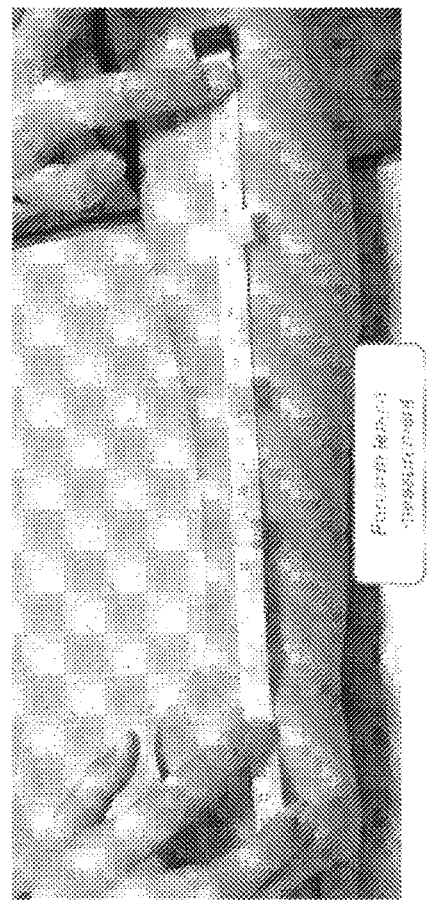

With reference now to FIG. 15, a non-limiting illustrative approach for fitting the sleeve 10 to a specific user is described. As shown in FIG. 15, the forearm length is measured from the wrist crease to the elbow crease, preferably with the arm bent at around 90-120 degrees at the elbow. The wrist circumference is measured at the most distal crease. Additionally, the forearm circumference is measured at three equally spaced distances between the wrist and the elbow, as measured based on the forearm length. (These three measurement points are indicated by yellow tabs in the left-hand image of FIG. 15). Finally, the maximum forearm circumference is measured (regardless of where it occurs along the forearm).

Figure 16:
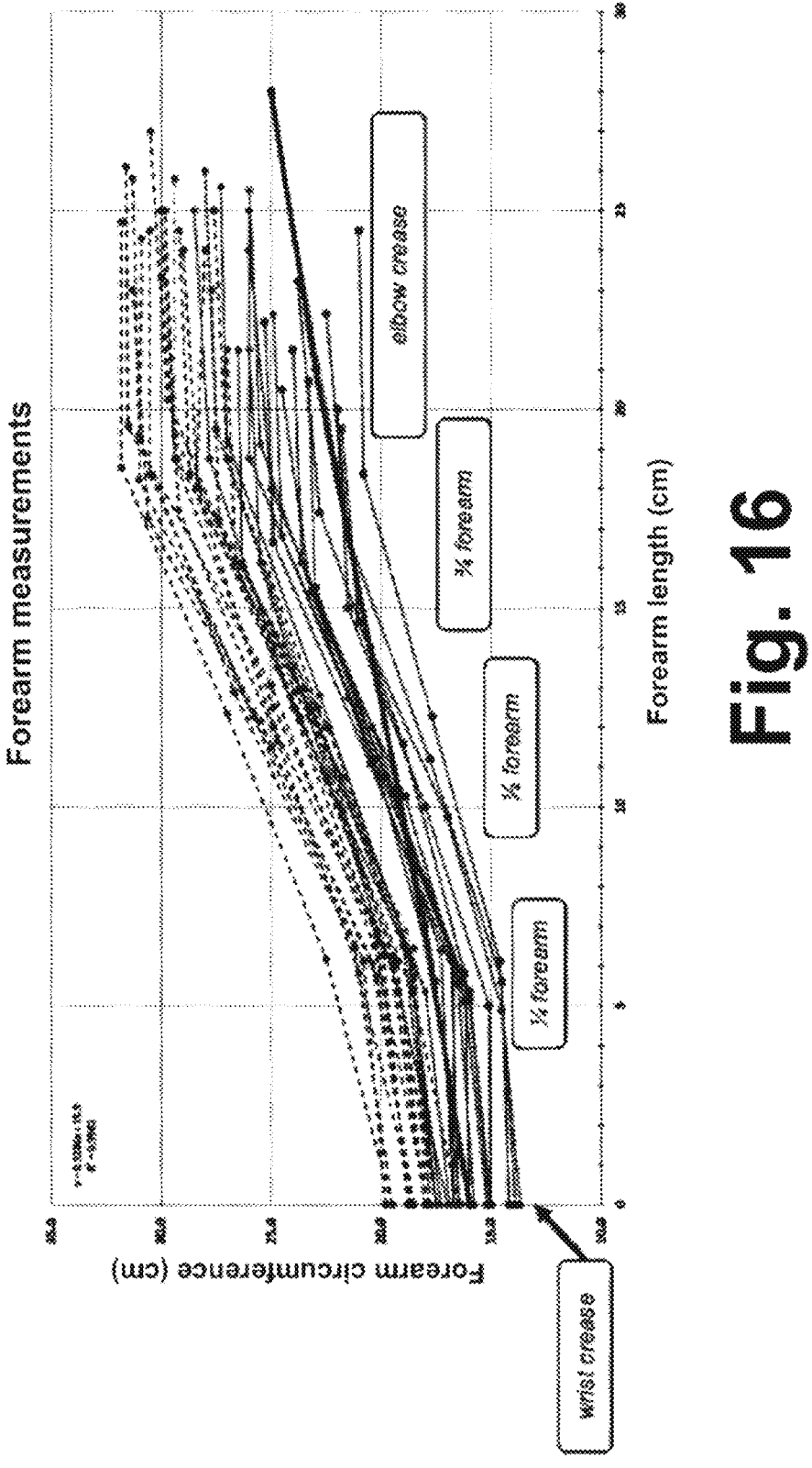
FIG. 16 plots the wrist circumference and three forearm circumference measurements as a function of position along the forearm (with the wrist at zero distance) for a number of measured individuals.

FIG. 16 plots the wrist circumference and three forearm circumference measurements as a function of position along the forearm (with the wrist at zero distance) for a number of measured individuals. Based on these measurements, it is seen that there is a generally common shape, in which the rate of increase in circumference from the wrist to the first forearm measurement (labeled ¼ forearm) is smaller than the rate of increase in circumference from the first forearm measurement (labeled ¼ forearm) to the second and third forearm measurements (labeled ½ forearm and ¾ forearm). Finally, the rate of increase in circumference between the third forearm measurement (labeled ¾ forearm) to the elbow is again small. Based on such measurements, in some embodiments the sleeve 10 is designed to fit this non-uniform increase in circumference with increasing distance from the wrist. Additionally, it was found that snug fits were best obtained if the sleeve 10 was provided in three sizes: small, medium, and large.

Figure 17:
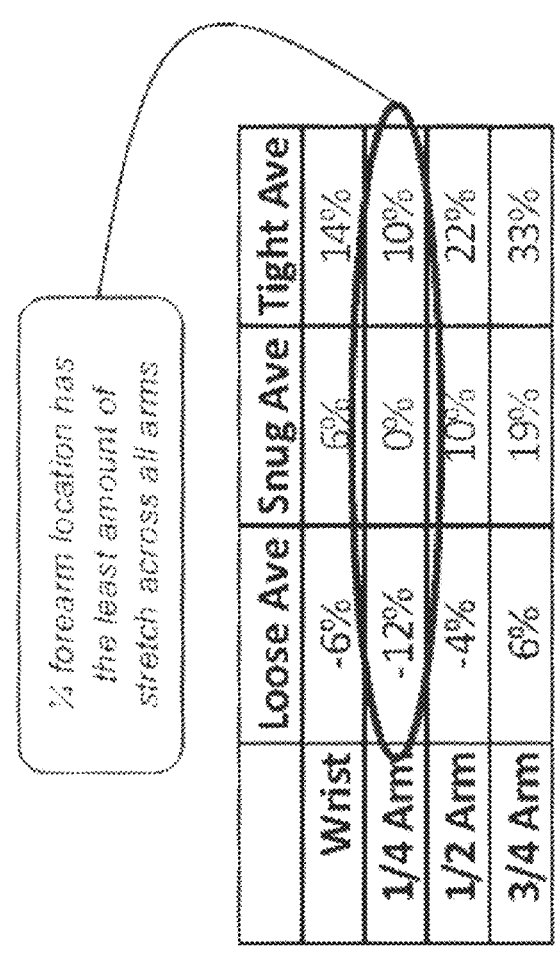
FIG. 17 presents a table of stretch percentage of the sleeve calculated for all forearm circumference measurements of FIG. 16, and then grouped by fit assessment (loose fit, snug fit, or tight fit).

With reference to FIG. 17, the stretch percentage of the sleeve was calculated for all forearm circumference measurements of FIG. 16, and then grouped by fit assessment (loose fit, snug fit, or tight fit) and presented as the table of FIG. 17. It was found that the ¼ forearm location has the least amount of stretch across all arms. On the other hand, tight fits could produce stretch percentages at the wrist of around 14%, and as high as around 25% or more at the ½ arm and ¾ arm positions. Hence, it was found that the sleeve 10 should be made of a fabric having a stretch percentage, e.g. in some embodiments in the range 7% to 25% inclusive.

Figure 18:
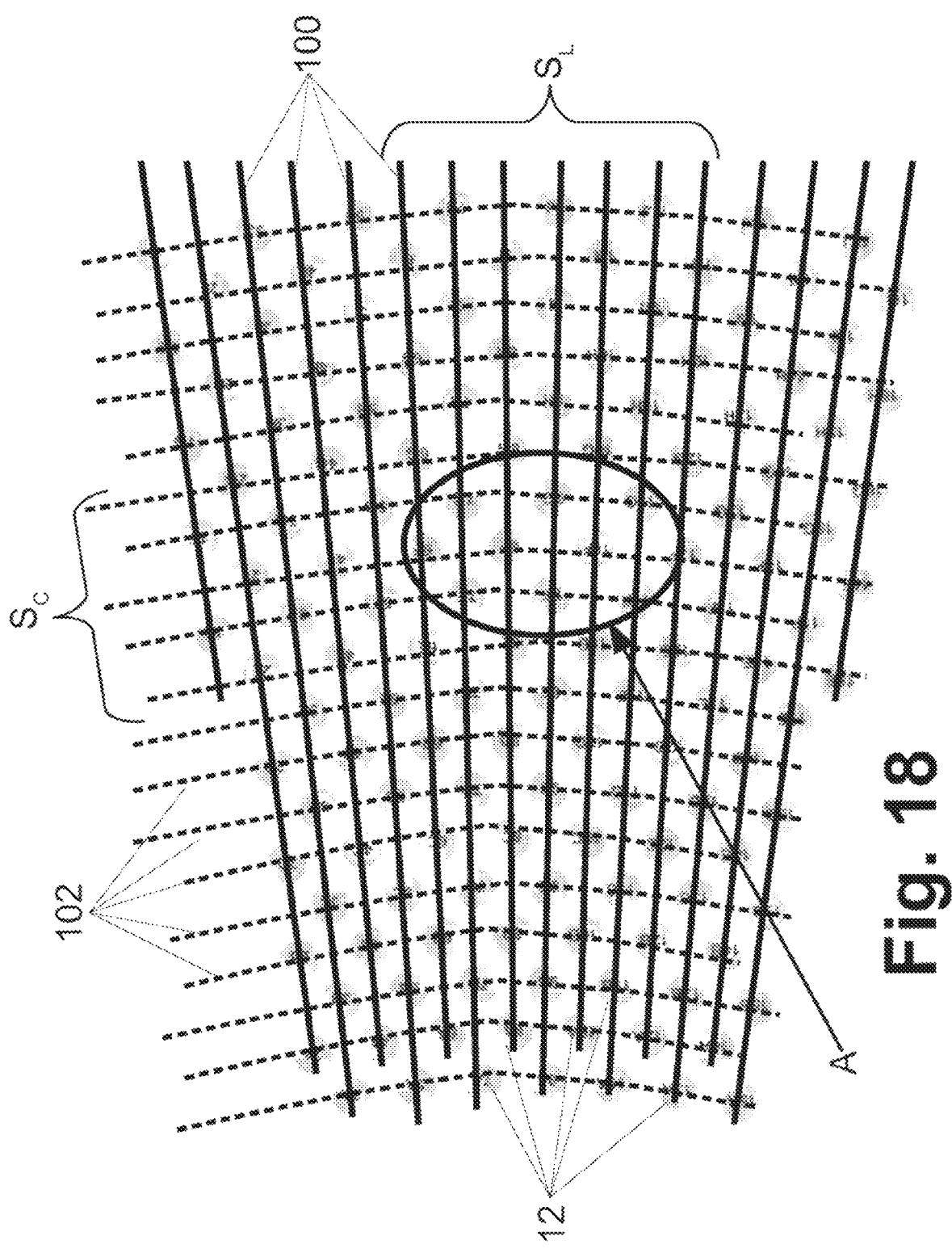
FIG. 18 diagrammatically shows an approach for energizing a high density of electrodes of the sleeve of FIG. 1.

With reference now to FIG. 18, an approach is described for obtaining a higher density of electrodes 12, which in turn permits stimulation at more precise locations due to the higher density of electrodes 12. In this approach, the electrodes 12 are electrically connected using an XY matrix of conductors, including longitudinal conductors 100 running longitudinally along the sleeve, and circumferential conductors 102 running circumferentially around the sleeve. This thus forms rows and columns. Operation is similar to a "reverse" touch screen, in which areas are energized by energizing those longitudinal and circumferential conductors that cross in that area. For example, an area A indicated in FIG. 18 would be energized by simultaneously energizing a set $S_L$ of the longitudinal conductors 100 and a set $S_C$ of the circumferential conductors 102. With a higher density of electrodes, the area A can be more precisely defined. Furthermore, due to the higher density of electrodes and the need for crossing conductors 100, 102 in this design, the circuit boards 62 are preferably replaced by electrically conductive yarn, stretch boards, or the like to enable the conductors 100, 102 to be highly flexible.

The illustrative embodiments are directed to arm sleeves extending over the forearm from (or above) the elbow to (or over) the wrist. More generally, the arm sleeves may additionally or alternatively extend over the upper arm and/or wrist. Even more generally, the device may comprise a wearable garment, such as the illustrative sleeve, a legging that is worn on the leg of the person, a wearable vest or chest band that is worn on the torso and/or abdomen of the person, and/or so forth. It is contemplated for the garment to cover multiple limbs, e.g. left and right sleeves left and right arms, respectively, which are connected to a common electronics module 48 to provide coordinated FES, NMES, or EMG readout for both left and right arms.

The disclosed sleeve or other wearable garment may be employed for various tasks, such as providing somatosensation to enhance the immersive environment in virtual reality (VR) or augmented reality (AR) systems, to provide somatosensation and/or force feedback in gaming systems, to provide NMES or FES for providing medical therapy to stroke victims, persons with partial or total paralysis due to a spinal cord injury, and/or so forth, and/or to provide EMG monitoring of musculature affected by such medical conditions, and/or so forth.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A device for use in performing functional electrical stimulation (FES), in performing neuromuscular electrical stimulation (NMES), and/or in receiving electromyography EMG) signals, the device comprising:

a sleeve sized and shaped to be worn on a human arm;

electrodes secured with the sleeve and positioned to contact skin of the human arm when the sleeve is worn on the human arm; and an electronic circuit configured to operate the electrodes, the electronic circuit including:

relays connecting the electrodes with a stimulator for performing FES or NMES, and EMG readout circuitry connecting the electrodes with an EMG amplifier, the EMG readout circuitry including field-effective transistor (FETs) which are on during EMG readout to connect the EMG amplifier with the electrodes and are off during FES or NMES to protect the EMG amplifier from voltages applied by the stimulator during FES or NMES, and pulling field-effect transistors (FETs) having terminals connected with ground, the pulling FETs being off during EMG readout to provide electrical continuity between the electrodes and the EMG amplifier and being on during FES or NMES to protect the EMG amplifier from voltages applied by the stimulator during FES or NMES; and wherein the relays are closed during FES or NMES to connect the stimulator with the electrodes, and the relays are open during EMG readout to isolate the stimulator from the EMG amplifier.

2. The device of claim 1 wherein the EMG readout circuitry includes a differential amplifier with a high pass filter.

3. The device of claim 2 wherein the high pass filter comprises a Chebyshev high pass filter.

4. The device of claim 1 further comprising:

an electronic module disposed on the sleeve and comprising at least the EMG readout circuitry.

5. The device of claim 4 wherein the electronic module disposed on the sleeve does not comprise the relays.

6. The device of claim 1 further comprising:
longitudinal conductors; and
circumferential conductors;
wherein a selected area is energized by energizing the set
of the longitudinal conductors and the set of the circumferential conductors that cross in the selected area.

7. The device of claim 1 further comprising optical
emitters arranged to optically control the relays.

8. The device of claim 1 further comprising electrostatic
discharge (ESD) suppressors connected to protect the electrodes from electrostatic discharge.

9. A method of performing functional electrical stimula-
tion (FES) or neuromuscular electrical stimulation (NMES)
on muscles and also receiving electromyography (EMG)
signals from the muscles, the method comprising:
performing FES or NMES on the muscles including
turning field-effect transistors (FETs) off during the
FES or NMES to protect an EMG amplifier from
voltages applied by the stimulator during the FES or
NMES;
reading EMG signals from the muscles using the EMG
amplifier including turning the FETs on during the
reading of the EMG signals to connect the EMG
amplifier with the electrodes;
closing solid state relays during the FES or NMES to connect the stimulator with the electrodes;
opening the solid state relays during the reading of the
EMG signals to isolate the stimulator from the EMG
amplifier;
turning off pulling field-effect transistors (FETs) that have
terminals connected with ground during the reading of
EMG signals; and
turning on the pulling FETs during the performing of FES
or NMES.

10. The method of claim 9 wherein the reading of the
EMG signals includes high pass filtering the EMG signals
with a differential amplifier; and
amplifying the high pass filtered EMG signals with the
EMG amplifier.

11. The method of claim 10 wherein the high pass filtering uses a Chebyshev high pass filter.

12. A device for use in performing functional electrical
stimulation (FES), in performing neuromuscular electrical stimulation (NMES), and/or in receiving electromyography
(EMG) signals, the device comprising:
electrodes configured to be positioned to contact skin;
a stimulator;
an EMG amplifier; and
an electronic circuit configured to switch between:
a stimulation mode in which the electronic circuit
connects the stimulator with the electrodes to per-
form FES or NMES and electrically isolates the
EMG amplifier from the electrodes, and
an EMG readout mode in which the electronic circuit
disconnects the stimulator from the electrodes and
provides electrical continuity between the electrodes
and the EMG amplifier;
wherein the electronic circuit includes:
solid state relays that close in the stimulation mode to
connect the stimulator with the electrodes and that
open in the EMG readout mode to disconnect the
stimulator from the electrodes;
field effect transistors (FETs) that are off in the stimu-
lation mode to electrically isolate the EMG amplifier
from the electrodes and that are on in the EMG
readout mode to provide electrical continuity
between the electrodes and the EMG amplifier; and
pulling field-effect transistors (FETs) having terminals
connected with ground, the pulling FETs being off in
EMG readout mode to provide electrical continuity
between the electrodes and the EMG amplifier and
being on in stimulation mode to protect the EMG
amplifier from voltages applied by the stimulator
during FES or NMES.

13. The device of claim 12 wherein the electronic circuit
includes a high pass filter operative to filter EMG signals
detected by the electrodes when the electronic circuit is in
the EMG readout mode.

14. The device of claim 13 wherein the high pass filter
comprises a Chebyshev high pass filter.

15. The device of claim 12 further comprising:
a garment including the electrodes and configured to be
worn on a person with the electrodes positioned to
contact the skin of the person.

* * * * *